(12) United States Patent
Sharma et al.

(10) Patent No.: US 11,839,714 B2
(45) Date of Patent: Dec. 12, 2023

(54) HEAT UNITS USING A SOLID FUEL CAPABLE OF UNDERGOING AN EXOTHERMIC METAL OXIDATION-REDUCTION REACTION PROPAGATED WITHOUT AN IGNITER

(71) Applicant: Alexza Pharmaceuticals, Inc., Mountain View, CA (US)

(72) Inventors: Krishnamohan Sharma, Milpitas, CA (US); Mingzu Lei, San Jose, CA (US)

(73) Assignee: ALEXZA PHARMACEUTICALS, INC., Mountain View, CA (US)

( * ) Notice: Subject to any disclaimer, the term of this patent is extended or adjusted under 35 U.S.C. 154(b) by 0 days.

(21) Appl. No.: 17/970,870

(22) Filed: Oct. 21, 2022

(65) Prior Publication Data

US 2023/0044017 A1 Feb. 9, 2023

Related U.S. Application Data

(63) Continuation of application No. 17/035,641, filed on Sep. 28, 2020, now Pat. No. 11,484,668, which is a
(Continued)

(51) Int. Cl.
*A61M 11/04* (2006.01)
*A61M 15/00* (2006.01)
(Continued)

(52) U.S. Cl.
CPC ......... *A61M 11/041* (2013.01); *A61M 11/047* (2014.02); *A61M 15/0051* (2014.02);
(Continued)

(58) Field of Classification Search
CPC ................. F42B 3/11; F42B 3/006; F24J 1/00
(Continued)

(56) References Cited

U.S. PATENT DOCUMENTS 3,150,020 A 9/1964 Kilmer
3,695,179 A 10/1972 Rainone
(Continued)

FOREIGN PATENT DOCUMENTS

CN 1514719 A 7/2004
CN 1700934 A 11/2005
(Continued)

OTHER PUBLICATIONS

U.S. Appl. No. 12/628,949, filed Dec. 1, 2009, Zaffaroni.
(Continued)

*Primary Examiner* — Vivek K Shirsat
(74) *Attorney, Agent, or Firm* — Quarles & Brady LLP

(57) ABSTRACT

A heating unit comprising an electrically conductive substrate. A solid fuel layer comprising a metal reducing agent, a metal containing oxidizing agent and a binder is coated on a surface of the substrate, the solid fuel layer having a solid fuel surface spaced from the substrate. A first electrode coupled to the substrate. A second electrode coupled to the solid fuel surface. A power supply is configured to be selectively coupled to the first and second electrodes to provide a voltage between the metallic substrate and the solid fuel surface. The voltage acts to propagate an exothermic metal oxidation-reduction reaction without the use of an igniter.

4 Claims, 11 Drawing Sheets

Related U.S. Application Data continuation of application No. 15/712,468, filed on Sep. 22, 2017, now Pat. No. 10,786,635, which is a continuation of application No. 13/217,385, filed on Aug. 25, 2011, now abandoned.

(60) Provisional application No. 61/377,377, filed on Aug. 26, 2010.

(51) Int. Cl.
    *F24V 30/00*     (2018.01)
    *A61M 5/44*     (2006.01)
    *A61M 15/06*     (2006.01)

(52) U.S. Cl.
    CPC ............ *F24V 30/00* (2018.05); *A61M 5/44* (2013.01); *A61M 15/06* (2013.01); *A61M 2205/364* (2013.01); *A61M 2205/8268* (2013.01); *Y10T 29/49117* (2015.01)

(58) Field of Classification Search
    USPC ......... 126/263.01–263.9; 431/262, 269, 361; 327/525; 102/202.5, 202.9, 202.11, 102/202.12
See application file for complete search history.

(56) References Cited

U.S. PATENT DOCUMENTS

| | | |
|---|---|---|
| 3,791,302 A | 2/1974 | McLeod |
| 3,792,302 A | 2/1974 | Downing |
| 3,831,606 A | 8/1974 | Damani |
| 3,882,323 A | 5/1975 | Smolker |
| 3,971,377 A | 7/1976 | Damani |
| 3,982,095 A | 9/1976 | Robinson |
| 4,013,061 A | 3/1977 | Trumble |
| 4,020,379 A | 4/1977 | Manning |
| 4,045,156 A | 8/1977 | Chu |
| 4,047,483 A | 9/1977 | Williams |
| 4,059,388 A | 11/1977 | Shaffer |
| 4,189,200 A | 2/1980 | Yeager |
| 4,193,388 A | 3/1980 | Frosch |
| 4,236,544 A | 12/1980 | Osaka |
| 4,354,432 A | 10/1982 | Cannavo |
| 4,369,269 A | 1/1983 | Harper |
| 4,372,213 A | 2/1983 | Rozner |
| 4,374,686 A | 2/1983 | Davitt |
| 4,419,650 A | 12/1983 | John |
| 4,443,495 A | 4/1984 | Morgan |
| 4,484,577 A | 11/1984 | Sackner |
| 4,508,755 A | 4/1985 | Reintjes |
| 4,627,963 A | 12/1986 | Olson |
| 4,700,629 A | 10/1987 | Benson |
| 4,708,151 A | 11/1987 | Shelar |
| 4,714,082 A | 12/1987 | Banerjee |
| 4,756,318 A | 7/1988 | Clearman |
| 4,793,366 A | 12/1988 | Hill |
| 4,819,665 A | 4/1989 | Roberts |
| 4,854,331 A | 8/1989 | Banerjee |
| 4,881,556 A | 11/1989 | Clearman |
| 4,892,037 A | 1/1990 | Betts |
| 4,922,901 A | 5/1990 | Brooks |
| 4,935,073 A | 6/1990 | Bartlett |
| 4,947,874 A | 8/1990 | Brooks |
| 4,947,875 A | 8/1990 | Brooks |
| 4,952,903 A | 8/1990 | Shibata |
| 4,989,619 A | 2/1991 | Clearman |
| 5,020,548 A | 6/1991 | Farrier |
| 5,027,707 A | 7/1991 | Mei |
| 5,033,483 A | 7/1991 | Clearman |
| 5,042,509 A | 8/1991 | Banerjee |
| 5,060,666 A | 10/1991 | Clearman |
| 5,060,671 A | 10/1991 | Counts |
| 5,067,499 A | 11/1991 | Banerjee |
| 5,095,921 A | 3/1992 | Loose |
| 5,105,831 A | 4/1992 | Banerjee |
| 5,135,009 A | 8/1992 | Muller |
| 5,144,962 A | 9/1992 | Counts |
| 5,179,966 A | 1/1993 | Losee |
| 5,224,498 A | 7/1993 | Deevi |
| 5,249,586 A | 10/1993 | Morgan |
| 5,269,327 A | 12/1993 | Counts |
| 5,285,798 A | 2/1994 | Banerjee |
| 5,322,018 A | 6/1994 | Hadden |
| 5,322,075 A | 6/1994 | Deevi |
| 5,345,951 A | 9/1994 | Serrano |
| 5,357,984 A | 10/1994 | Farrier |
| 5,407,473 A | 4/1995 | Miura |
| 5,408,574 A | 4/1995 | Deevi |
| 5,415,161 A | 5/1995 | Ryder |
| 5,468,936 A | 11/1995 | Deevi |
| 5,479,948 A | 1/1996 | Counts |
| 5,505,214 A | 4/1996 | Collins |
| 5,509,354 A | 4/1996 | Dorffler |
| 5,554,646 A | 5/1996 | Lloyd |
| 5,538,020 A | 7/1996 | Farrier |
| 5,549,849 A | 8/1996 | Namura |
| 5,564,442 A | 10/1996 | MacDonald |
| 5,573,565 A | 11/1996 | Dalton |
| 5,584,701 A | 12/1996 | Lampotang |
| 5,591,368 A | 1/1997 | Fleischhauer |
| 5,593,792 A | 1/1997 | Farrier |
| 5,601,073 A | 2/1997 | Shimek |
| 5,603,350 A | 2/1997 | Stoll |
| 5,613,504 A | 3/1997 | Collins |
| 5,613,505 A | 3/1997 | Campbell |
| 5,623,115 A | 4/1997 | Lauritzen |
| 5,626,360 A | 5/1997 | Lauritzen |
| 5,649,554 A | 7/1997 | Sprinkel |
| 5,672,843 A | 9/1997 | Evans |
| 5,686,691 A | 11/1997 | Hamilton |
| 5,694,919 A | 12/1997 | Rubsamen |
| 5,705,261 A | 1/1998 | Axelson |
| 5,735,263 A | 4/1998 | Rubsamen |
| 5,845,578 A | 12/1998 | Fogle, Jr. |
| 5,845,933 A | 12/1998 | Walker |
| 5,853,810 A | 12/1998 | Zhang et al. |
| 5,865,185 A | 2/1999 | Collins |
| 5,878,752 A | 3/1999 | Adams |
| 5,890,908 A | 4/1999 | Lampotang |
| 5,906,281 A | 5/1999 | Fujikawa |
| 5,915,378 A | 6/1999 | Lloyd |
| 5,934,272 A | 8/1999 | Lloyd |
| 5,957,124 A | 9/1999 | Lloyd |
| 5,960,792 A | 10/1999 | Lloyd |
| 6,014,970 A | 1/2000 | Ivri |
| 6,053,176 A | 4/2000 | Adams |
| 6,062,210 A | 5/2000 | Welles |
| 6,090,403 A | 7/2000 | Block |
| 6,095,153 A | 8/2000 | Kessler |
| 6,102,036 A | 8/2000 | Slutsky |
| 6,164,287 A | 12/2000 | White |
| 6,190,326 B1 | 2/2001 | McKinnon |
| 6,289,813 B1 | 9/2001 | Duguet |
| 6,325,475 B1 | 12/2001 | Hayes |
| 6,328,033 B1 | 12/2001 | Avrahami |
| 6,390,453 B1 | 5/2002 | Frederickson |
| 6,478,903 B1 | 11/2002 | John |
| 6,632,380 B1 | 10/2003 | Wessling |
| 6,648,950 B2 | 11/2003 | Lee |
| 6,660,632 B2 | 12/2003 | Hill |
| 6,671,945 B2 | 1/2004 | Gerber |
| 6,680,668 B2 | 1/2004 | Gerber |
| 6,682,716 B2 | 1/2004 | Hodges |
| 6,684,880 B2 | 2/2004 | Trueba |
| 6,713,399 B1 | 3/2004 | Kao |
| 6,716,415 B2 | 4/2004 | Rabinowitz |
| 6,716,416 B2 | 4/2004 | Rabinowitz |
| 6,716,417 B2 | 4/2004 | Rabinowitz |
| 6,737,042 B2 | 5/2004 | Rabinowitz |
| 6,737,043 B2 | 5/2004 | Rabinowitz |
| 6,740,307 B2 | 5/2004 | Rabinowitz |
| 6,740,308 B2 | 5/2004 | Rabinowitz |
| 6,740,309 B2 | 5/2004 | Rabinowitz |

(56) References Cited

U.S. PATENT DOCUMENTS

| | | |
|---|---|---|
| 6,743,415 B2 | 6/2004 | Rabinowitz |
| 6,759,029 B2 | 7/2004 | Hale |
| 6,776,978 B2 | 8/2004 | Rabinowitz |
| 6,780,399 B2 | 8/2004 | Rabinowitz |
| 6,780,400 B2 | 8/2004 | Rabinowitz |
| 6,783,753 B2 | 8/2004 | Rabinowitz |
| 6,797,259 B2 | 9/2004 | Rabinowitz |
| 6,803,031 B2 | 10/2004 | Rabinowitz |
| 6,805,853 B2 | 10/2004 | Rabinowitz |
| 6,805,854 B2 | 10/2004 | Hale |
| 6,812,432 B1 | 11/2004 | Haluschka |
| 6,814,954 B2 | 11/2004 | Rabinowitz |
| 6,814,955 B2 | 11/2004 | Rabinowitz |
| 6,855,310 B2 | 2/2005 | Rabinowitz |
| 6,884,408 B2 | 4/2005 | Rabinowitz |
| 6,994,843 B2 | 2/2006 | Rabinowitz |
| 7,005,121 B2 | 2/2006 | Rabinowitz |
| 7,005,122 B2 | 2/2006 | Hale |
| 7,008,615 B2 | 3/2006 | Rabinowitz |
| 7,008,616 B2 | 3/2006 | Rabinowitz |
| 7,011,819 B2 | 3/2006 | Hale |
| 7,011,820 B2 | 3/2006 | Rabinowitz |
| 7,014,840 B2 | 3/2006 | Hale |
| 7,014,841 B2 | 3/2006 | Rabinowitz |
| 7,018,619 B2 | 3/2006 | Rabinowitz |
| 7,018,620 B2 | 3/2006 | Rabinowitz |
| 7,018,621 B2 | 3/2006 | Hale |
| 7,022,312 B2 | 4/2006 | Rabinowitz |
| 7,029,658 B2 | 4/2006 | Rabinowitz |
| 7,033,575 B2 | 4/2006 | Rabinowitz |
| 7,045,118 B2 | 5/2006 | Rabinowitz |
| 7,045,119 B2 | 5/2006 | Rabinowitz |
| 7,048,909 B2 | 5/2006 | Rabinowitz |
| 7,052,679 B2 | 5/2006 | Rabinowitz |
| 7,052,680 B2 | 5/2006 | Rabinowitz |
| 7,060,254 B2 | 6/2006 | Rabinowitz |
| 7,060,255 B2 | 6/2006 | Rabinowitz |
| 7,063,830 B2 | 6/2006 | Rabinowitz |
| 7,063,831 B2 | 6/2006 | Rabinowitz |
| 7,063,832 B2 | 6/2006 | Rabinowitz |
| 7,067,114 B2 | 6/2006 | Rabinowitz |
| 7,070,761 B2 | 7/2006 | Rabinowitz |
| 7,070,762 B2 | 7/2006 | Rabinowitz |
| 7,070,763 B2 | 7/2006 | Rabinowitz |
| 7,070,764 B2 | 7/2006 | Rabinowitz |
| 7,070,765 B2 | 7/2006 | Rabinowitz |
| 7,070,766 B2 | 7/2006 | Rabinowitz |
| 7,078,016 B2 | 7/2006 | Rabinowitz |
| 7,078,017 B2 | 7/2006 | Rabinowitz |
| 7,078,018 B2 | 7/2006 | Rabinowitz |
| 7,078,019 B2 | 7/2006 | Rabinowitz |
| 7,078,020 B2 | 7/2006 | Rabinowitz |
| 7,087,216 B2 | 8/2006 | Rabinowitz |
| 7,087,217 B2 | 8/2006 | Rabinowitz |
| 7,087,218 B2 | 8/2006 | Rabinowitz |
| 7,090,830 B2 | 8/2006 | Hale |
| 7,094,392 B2 | 8/2006 | Rabinowitz |
| 7,108,847 B2 | 9/2006 | Rabinowitz |
| 7,115,250 B2 | 10/2006 | Rabinowitz |
| 7,169,378 B2 | 1/2007 | Rabinowitz |
| 7,402,777 B2 | 7/2008 | Hale |
| 7,442,368 B2 | 10/2008 | Rabinowitz |
| 7,445,768 B2 | 11/2008 | Rabinowitz |
| 7,449,172 B2 | 11/2008 | Rabinowitz |
| 7,449,173 B2 | 11/2008 | Rabinowitz |
| 7,449,174 B2 | 11/2008 | Rabinowitz |
| 7,449,175 B2 | 11/2008 | Rabinowitz |
| 7,458,374 B2 | 12/2008 | Hale |
| 7,465,435 B2 | 12/2008 | Rabinowitz |
| 7,465,436 B2 | 12/2008 | Rabinowitz |
| 7,465,437 B2 | 12/2008 | Rabinowitz |
| 7,468,179 B2 | 12/2008 | Rabinowitz |
| 7,470,421 B2 | 12/2008 | Rabinowitz |
| 7,485,285 B2 | 2/2009 | Rabinowitz |
| 7,488,469 B2 | 2/2009 | Rabinowitz |
| 7,491,047 B2 | 2/2009 | Rabinowitz |
| 7,494,344 B2 | 2/2009 | Galauner |
| 7,498,019 B2 | 3/2009 | Hale |
| 7,507,397 B2 | 3/2009 | Rabinowitz |
| 7,507,398 B2 | 3/2009 | Rabinowitz |
| 7,510,702 B2 | 3/2009 | Rabinowitz |
| 7,513,781 B2 | 4/2009 | Galauner |
| 7,524,484 B2 | 4/2009 | Rabinowitz |
| 7,537,009 B2 | 5/2009 | Hale |
| 7,540,286 B2 | 6/2009 | Cross |
| 7,550,133 B2 | 6/2009 | Hale |
| 7,581,540 B2 | 9/2009 | Hale |
| 7,585,493 B2 | 9/2009 | Hale |
| 7,601,337 B2 | 10/2009 | Rabinowitz |
| 7,645,442 B2 | 1/2010 | Hale |
| 7,766,013 B2 | 8/2010 | Wensley |
| 7,785,482 B2 | 8/2010 | Subramanian |
| 7,834,295 B2 | 11/2010 | Sharma |
| 7,913,688 B2 | 3/2011 | Cross |
| 7,923,662 B2 | 4/2011 | Hale |
| 7,942,147 B2 | 5/2011 | Hodges |
| 7,981,401 B2 | 7/2011 | Every |
| 7,987,846 B2 | 8/2011 | Hale |
| 7,988,952 B2 | 8/2011 | Rabinowitz |
| 8,003,080 B2 | 8/2011 | Rabinowitz |
| 8,074,644 B2 | 12/2011 | Hale |
| 8,173,107 B2 | 5/2012 | Rabinowitz |
| 8,235,037 B2 | 8/2012 | Hale |
| 8,288,372 B2 | 10/2012 | Hale |
| 8,333,197 B2 | 12/2012 | Cross |
| 8,387,612 B2 | 3/2013 | Damani |
| 8,425,704 B2 | 4/2013 | Currano |
| 8,506,935 B2 | 8/2013 | Hale |
| 8,955,512 B2 | 2/2015 | Hale |
| 8,991,387 B2 | 3/2015 | Damani |
| 9,211,382 B2 | 12/2015 | Hale |
| 9,308,208 B2 | 4/2016 | Wensley |
| 9,370,629 B2 | 6/2016 | Damani |
| 9,439,907 B2 | 9/2016 | Hale |
| 9,440,034 B2 | 9/2016 | Hale |
| 9,687,487 B2 | 6/2017 | Hodges |
| 9,724,341 B2 | 8/2017 | Myers |
| 10,166,224 B2 | 1/2019 | Myers |
| 10,350,157 B2 | 7/2019 | Hale |
| 10,625,033 B2 | 4/2020 | Wensley |
| 10,786,635 B2 | 9/2020 | Sharma |
| 11,484,668 B2 * | 11/2022 | Sharma ............... A61M 11/047 |
| 2002/0000225 A1 | 1/2002 | Schuler |
| 2002/0035945 A1 | 3/2002 | Knowlton |
| 2002/0036192 A1 | 3/2002 | Sato |
| 2002/0037437 A1 | 3/2002 | Yamamoto |
| 2002/0097139 A1 | 7/2002 | Gerber |
| 2002/0185485 A1 | 12/2002 | Radmacher |
| 2003/0032638 A1 | 2/2003 | Kim |
| 2003/0049025 A1 | 3/2003 | Neumann |
| 2003/0051728 A1 | 3/2003 | Lloyd |
| 2003/0070738 A1 | 4/2003 | Hamilton |
| 2003/0118512 A1 | 6/2003 | Shen |
| 2003/0121906 A1 | 7/2003 | Abbott |
| 2003/0131843 A1 | 7/2003 | Lu |
| 2003/0138508 A1 | 7/2003 | Novack |
| 2003/0145924 A1 | 8/2003 | Carter, Jr. |
| 2004/0001048 A1 | 1/2004 | Kraus |
| 2004/0016427 A1 | 1/2004 | Byron |
| 2004/0035409 A1 | 2/2004 | Harwig |
| 2004/0055504 A1 | 3/2004 | Lee |
| 2004/0083919 A1 | 5/2004 | Hosey |
| 2004/0096402 A1 | 5/2004 | Hodges |
| 2004/0099269 A1 | 5/2004 | Hale |
| 2004/0101481 A1 | 5/2004 | Hale |
| 2004/0102434 A1 | 5/2004 | Hale |
| 2004/0105818 A1 | 6/2004 | Every |
| 2004/0162517 A1 | 8/2004 | Furst |
| 2004/0234699 A1 | 11/2004 | Hale |
| 2004/0234914 A1 | 11/2004 | Hale |
| 2004/0234916 A1 | 11/2004 | Hale |
| 2005/0034723 A1 | 2/2005 | Bennett |
| 2005/0037506 A1 | 2/2005 | Hale |
| 2005/0079166 A1 | 4/2005 | Damani |

(56) References Cited

U.S. PATENT DOCUMENTS

| | | |
|---|---|---|
| 2005/0126562 A1 | 6/2005 | Rabinowitz |
| 2005/0131739 A1 | 6/2005 | Rabinowitz |
| 2006/0032496 A1 | 2/2006 | Hale |
| 2006/0120962 A1 | 6/2006 | Rabinowitz |
| 2006/0148970 A1 | 7/2006 | Kuba |
| 2006/0193788 A1 | 8/2006 | Hale |
| 2006/0257329 A1 | 11/2006 | Rabinowitz |
| 2007/0122353 A1 | 5/2007 | Hale |
| 2007/0286816 A1 | 12/2007 | Hale |
| 2008/0038363 A1 | 2/2008 | Zaffaroni |
| 2008/0210225 A1 | 9/2008 | Geiger |
| 2008/0216828 A1 | 9/2008 | Wensley |
| 2008/0257345 A1 | 10/2008 | Snyder |
| 2008/0299048 A1 | 12/2008 | Hale |
| 2008/0306285 A1 | 12/2008 | Hale |
| 2008/0311176 A1 | 12/2008 | Hale |
| 2009/0062254 A1 | 3/2009 | Hale |
| 2009/0180968 A1 | 7/2009 | Hale |
| 2009/0229600 A1 | 9/2009 | Hale |
| 2009/0235926 A1 | 9/2009 | Cross |
| 2009/0246147 A1 | 10/2009 | Rabinowitz |
| 2009/0258075 A1 | 10/2009 | Hale |
| 2009/0301363 A1 | 12/2009 | Damani |
| 2010/0006092 A1 | 1/2010 | Hale |
| 2010/0055048 A1 | 3/2010 | Hale |
| 2010/0065052 A1 | 3/2010 | Sharma |
| 2010/0068155 A1 | 3/2010 | Lei |
| 2010/0181387 A1 | 7/2010 | Zaffaroni |
| 2010/0208438 A1 | 8/2010 | Kaltenbacher |
| 2010/0294268 A1 | 11/2010 | Wensley |
| 2010/0300433 A1 | 12/2010 | Sharma |
| 2011/0233043 A1 | 9/2011 | Cross |
| 2011/0240013 A1 | 10/2011 | Hale |
| 2011/0240014 A1 | 10/2011 | Bennett |
| 2011/0240022 A1 | 10/2011 | Hodges |
| 2011/0244020 A1 | 10/2011 | Hale |
| 2011/0245493 A1 | 10/2011 | Rabinowitz |
| 2011/0253135 A1 | 10/2011 | Hale |
| 2012/0048963 A1 | 3/2012 | Sharma |
| 2013/0032139 A1 | 2/2013 | Hale |
| 2013/0180525 A1 | 7/2013 | Cross |
| 2013/0276781 A1 | 10/2013 | Steelman |
| 2014/0060525 A1 | 3/2014 | Hale |
| 2014/0060532 A1 | 3/2014 | Hodges |
| 2014/0066618 A1 | 3/2014 | Hale |
| 2014/0072605 A1 | 3/2014 | Bennett |
| 2015/0157635 A1 | 6/2015 | Hale |
| 2015/0250800 A1 | 9/2015 | Hale |
| 2015/0265783 A1 | 9/2015 | Damani |
| 2016/0166564 A1 | 6/2016 | Myers |
| 2016/0324845 A1 | 11/2016 | Myers |
| 2016/0374937 A1 | 12/2016 | Hale |
| 2017/0049974 A1 | 2/2017 | Wensley |
| 2017/0105246 A1 | 4/2017 | Cross |
| 2017/0281884 A1 | 10/2017 | Hodges |
| 2018/0021328 A1 | 1/2018 | Myers |
| 2018/0126098 A1 | 5/2018 | Sharma |
| 2019/0021987 A1 | 1/2019 | Sharma |
| 2019/0117909 A1 | 4/2019 | Myers |
| 2019/0209546 A1 | 7/2019 | Myers |
| 2019/0307680 A1 | 10/2019 | Cassella |
| 2020/0246559 A1 | 8/2020 | Wensley |
| 2021/0008300 A1 | 1/2021 | Sharma |
| 2021/0046259 A1 | 2/2021 | Hasegawa |
| 2021/0052830 A1 | 2/2021 | Myers |

FOREIGN PATENT DOCUMENTS

| | | |
|---|---|---|
| CN | 1990057 A | 7/2007 |
| DE | 3542447 A1 | 6/1987 |
| EP | 0277519 | 8/1988 |
| EP | 279796 A1 | 8/1988 |
| EP | 0358114 | 3/1990 |
| EP | 0430559 | 6/1991 |
| EP | 816674 A1 | 1/1998 |
| GB | 2049651 A | 12/1980 |
| JP | 2006-523486 | 10/2006 |
| JP | 6773675 | 10/2020 |
| KR | 10-2217768 | 2/2021 |
| WO | WO 1993/011817 | 6/1993 |
| WO | WO 1994/009842 | 5/1994 |
| WO | WO 1994/027653 | 12/1994 |
| WO | WO 1996/009846 | 4/1996 |
| WO | WO 1996/013161 | 5/1996 |
| WO | WO 1996/013290 | 5/1996 |
| WO | WO 1996/013291 | 5/1996 |
| WO | WO 1996/013292 | 5/1996 |
| WO | WO 1996/030068 | 10/1996 |
| WO | WO 1997/027804 | 8/1997 |
| WO | WO 1998/022170 | 5/1998 |
| WO | WO 1998/036651 | 8/1998 |
| WO | WO 1999/064094 | 12/1999 |
| WO | WO 2000/029053 | 5/2000 |
| WO | WO 2000/066084 | 11/2000 |
| WO | WO 2000/066206 | 11/2000 |
| WO | WO 2000/076673 | 12/2000 |
| WO | WO 2001/005459 | 1/2001 |
| WO | WO 2002/094218 | 11/2002 |
| WO | WO 2002/094236 | 11/2002 |
| WO | WO 2002/094242 | 11/2002 |
| WO | WO 2003/037412 | 5/2003 |
| WO | WO 2003/094900 | 11/2003 |
| WO | WO 2003/095012 | 11/2003 |
| WO | WO 2004/091704 | 10/2004 |
| WO | WO 2004/104490 | 12/2004 |
| WO | WO 2004/104491 | 12/2004 |
| WO | WO 2004/104492 | 12/2004 |
| WO | WO 2004/104493 | 12/2004 |
| WO | WO 2004/106268 | 12/2004 |
| WO | WO 2005/120614 | 12/2005 |
| WO | WO 2012/026963 | 3/2012 |
| WO | WO 2016/145075 | 9/2016 |

OTHER PUBLICATIONS

U.S. Appl. No. 13/078,516, filed Apr. 1, 2011, Hale.
U.S. Appl. No. 13/078,519, filed Apr. 1, 2011, Hale.
U.S. Appl. No. 13/078,525, filed Apr. 1, 2011, Rainbow.
U.S. Appl. No. 13/078,600, filed Apr. 1, 2011, Hodges.
U.S. Appl. No. 13/078,606, filed Apr. 1, 2011, Hale.
U.S. Appl. No. 13/078,654, filed Apr. 1, 2011, Cross.
U.S. Appl. No. 13/078,668, filed Apr. 1, 2011, Bennett.
U.S. Appl. No. 13/217,385, filed Aug. 25, 2011, Sharma.
U.S. Appl. No. 13/311,660, filed Dec. 6, 2011, Bennett.
U.S. Appl. No. 13/597,865, filed Aug. 29, 2012, Bennett.
Alexza Pharmaceuticals (2015) "AZ-002 (Staccato alprazolam) in epilepsy patients", Dec. 21, 2015, p. 1-8.
Banhart (2000) "Manufacturing Routes for Metallic Foams" JOM, Dec. 2000:22-27.
Banhart (2001) Progress in Materials Science, 46:559-632 "Manufacture, characterization and application of cellular metals and metal foams".
Bennett et al. (1981) Annual Surg. 195(6):700-705 "Patient-Controlled Analgesia: A New Concept of Postoperative Pain Relief".
Bickes and Grubelich (1996) "SCB Ignition of Pyrotechnics, thermites, and intermetallics". Explosive Components Department, Sandia National Laboratories. Aug. 20, 1996.
Communication pursuant to Article 94(3) EPC from European App No. 16762425.3, dated Oct. 23, 2019, 8 pages.
Communication pursuant to Article 94(3) EPC from European App No. 16762425.3, dated Dec. 3, 2020, 6 pages.
Communication pursuant to Article 94(3) EPC from European App No. 16762425.3, dated Jul. 20, 2021, 6 pages.
Darquenne et al. (1997) American Physiological Society 83(3):966-974, "Aerosol Dispersion in Human Lung: Comparison Between Numerical Simulations and Experiments for Bolus Tests".
Davies et al. (1972) Journal of Applied Physiology 32(5):591-600, "Breathing of Half-Micron Aerosols".
Dershwitz et al. (2000) Anesthesiology 93(3): 619-628 "Pharmacokinetics and Pharmacodynamics of Inhaled versus Intravenous Morphine in Healthy Volunteers".

(56) References Cited

OTHER PUBLICATIONS

De Yong et al. (1998) Propellants, Explosives, Pyrotechnics 23:328-332 "Radiative Ignition of Pyrotechnics: Effect of Wavelength on Ignition Threshold".
Examination Report for Australian App No. 2016229119, dated Nov. 13, 2017, 4 pages.
Examination report 1 for Australia Application No. 2018264013, dated Feb. 20, 2020, 4 pages.
Examination Report (First) for New Zealand App No. 735414, dated Mar. 19, 2018, 7 pages.
Examination Report (Further) for New Zealand App No. 735414, dated Nov. 6, 2018, 3 pages.
Examination Report (Further) for New Zealand App No. 754325, dated May 3, 2021, 4 pages.
Examination Report (Further) for New Zealand App No. 751850, dated May 11, 2021, 5 pages.
Finlay (2001) "The Mechanics of Inhaled Pharmaceutical Aerosols", Academic Press: San Diego Formula 2.39. pp. 3-14 (Table of Contents). pp. v-viii.
Frieser et al. (1980) Journal of Applied Electrochemistry 10:449-457 "Surface treatments of silicon to enhance thermal nucleation".
Gonda (1991) "Particle Deposition in the Human Respiratory Tract," Chapter 176, The Lung: Scientific Foundations. Crystal R.G. and West, J.B. (eds.), Raven Publishers, New York. pp. 2289-2294.
Heyder et al. (1986) J. Aerosol Sci. 17(5):811-822 "Deposition of Particles in the Human Respiratory Tract in the Size Range 0.005-15 µm".
Hurt and Robertson (1998) JAMA 280(13):1173-1181 "Prying Open the Door to the Tobacco Industry's Secrets About Nicotine: The Minnesota Tobacco Trial".
International Preliminary Report on Patentability for PCT/US2016/021554, dated Sep. 12, 2017, 7 pages.
International Search Report and Written Opinion for PCT/US2016/021554, dated May 27, 2016.
Martin and Lue (May/Jun. 1989) Journal of Analytical Toxicology 13:158-162 "Pyrolysis and Volatilization of Cocaine".
McCarthy et al. (May 1985) Sandia Report "Burn Front Velocity as a function of Pellet Density in Iron /Potassium Perchlorate Heat Powders".
Merzhanov, Alexander G., (Aug. 19, 1994) Russian Academy of Sciences: International Pyrotechnics Seminar Colorado Springs, US Jul. 25-29, 1994 "Pyrotechnical Aspects of Self-Propogating High-Temperature Synthesis".
Office Action dated Jun. 22, 2018 with respect to Canadian App No. 2,979,213, 7 pages.
Office Action dated Apr. 2, 2019 with respect to Canadian App No. 2,979,213, 5 pages.
Office Action dated Feb. 3, 2020 with respect to Canadian App No. 2,979,213, 5 pages.
Office Action dated Nov. 29, 2019 with respect to Chinese App No. 201680027355.7 (w/English Translation), 15 pages.
Office Action dated Sep. 10, 2020 with respect to Chinese App No. 201680027355.7 (w/English Translation), 15 pages.
Office Action dated Feb. 22, 2022 with respect to Chinese App No. 202110917521.3 (w/English Translation), 11 pages.
Office Action dated Oct. 29, 2018 with respect to Japanese App No. 2017-548052 (w/English Translation), 13 pages.
Office Action dated Sep. 20, 2019 with respect to Japanese App No. 2017-548052 (w/English Translation), 6 pages.
Office Action dated Oct. 1, 2021 with respect to Japanese App No. 2020-166796 (w/English Translation), 6 pages.
Office Action dated Jan. 21, 2019 with respect to Korean App No. 10-2017-7028542 (w/English Translation) 15 pages.
Office Action dated Oct. 31, 2019 with respect to Korean App No. 10-2017-7028542 (w/English Translation) 13 pages.
Office Action dated Apr. 30, 2021 with respect to Korean App No. 10-2021-7004329 (w/English Translation), 12 pages.
Pankow et al. (1997) Environ. Sci. Technol. 31:2428-2433 "Conversion of Nicotine in Tobacco Smoke to Its Volatile and Available Free-Base Form through the Action of Gaseous Ammonia".
Pankow (2000) ACS Conference—San Francisco—Mar. 26, 2000, pp. 1-8 "Chemistry of Tobacco Smoke".
Peeters et al. (Jul. 1997) Circuits and Devices pp. 19-23 "Thermal Inkjet Technology".
Reticulated Carbon (1997) Flyer for ERG Materials and Aerospace Corp.
Search Report Supplementary from European Application No. 16762425.3, dated Nov. 2, 2018, 9 pages.
Seeman et al. (1999) J. Agric. Food Chem. 47(12):5133-5145 "The Form of Nicotine in Tobacco. Thermal Transfer of Nicotine and Nicotine Acid Salts to Nicotine in the Gas Phase".
Sekine and Nakahara (1987) Journal of Forensic Science 32(5):1271-1280 "Abuse of Smoking Methamphetamine Mixed with Tobacco: 1. Inhalation Efficiency and Pyrolysis Products of Methamphetamine".
Ward et al. (1997) Clinical Pharmacology & Therapeutics 62(6):596-609 "Morphine Pharmacokinetics after Pulmonary Administration from a Novel Aerosol Delivery System".
Welsher, et al., (1990) AT&T Technical Journal, May/June. "Design for Electrostatic Discharge (ESD) Protection in Telecommunications Products", 977-95.

\* cited by examiner

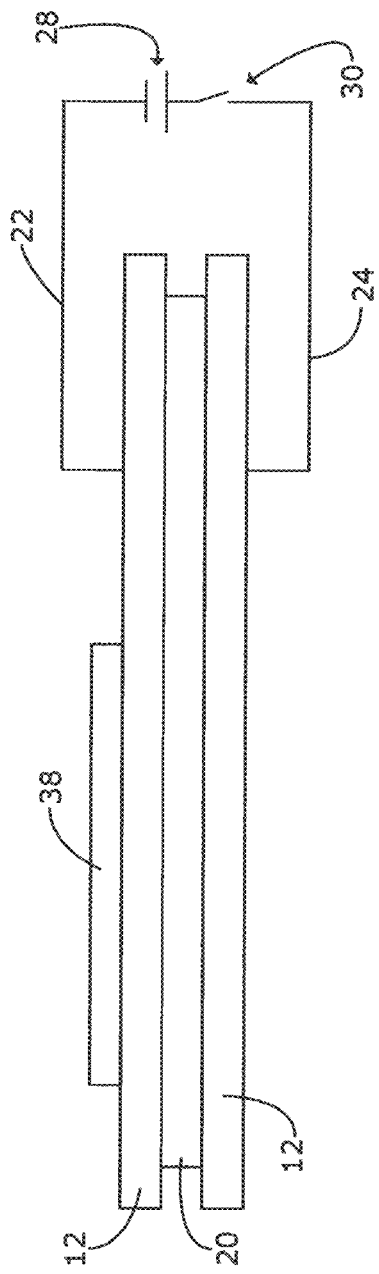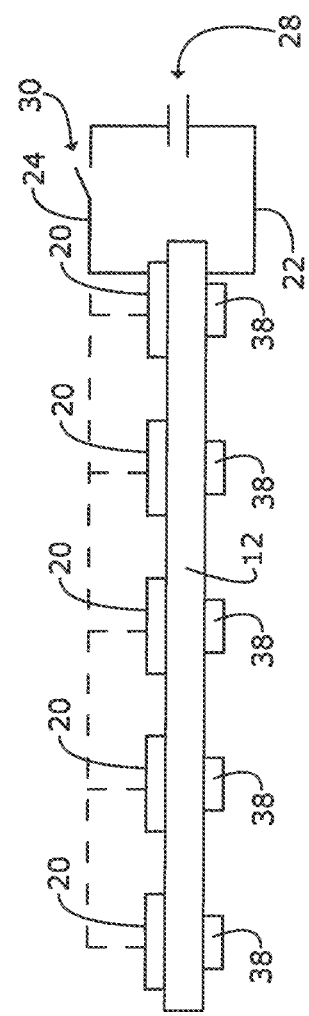

| Voltage (V) | Reactant Thickness per side (um) | Capacitor (uF) | Energy (mJ) |
|---|---|---|---|
| 5 | 20 | 330.0 | 4.125 |
|  | 28 | 220.0 | 2.750 |
|  | 42 | 100.0 | 1.250 |
|  | 45 | 22.0 | 0.275 |
| 10 | 26 | 22.0 | 1.100 |
|  | 29 | 47.0 | 2.350 |
|  | 30 | 22.0 | 1.100 |
|  | 39 | 10.0 | 0.500 |
|  | 47 | 10.0 | 0.500 |
| 15 | 21 | 33.0 | 3.713 |
|  | 30 | 10.0 | 1.125 |
|  | 38 | 10.0 | 1.125 |
|  | 47 | 10.0 | 1.125 |
|  | 49 | 100.0 | 11.250 |

| Voltage (V) | Reactant Thickness per side (um) | Capacitor (uF) | Energy (mJ) |
|---|---|---|---|
| 20 | 23 | 47.0 | 9.400 |
|  | 33 | 10.0 | 2.000 |
|  | 37 | 22.0 | 4.400 |
|  | 41 | 10.0 | 2.000 |
|  | 47 | 1.0 | 0.200 |
| 25 | 23 | 22.0 | 6.875 |
|  | 32 | 22.0 | 6.875 |
|  | 35 | 10.0 | 3.125 |
|  | 36 | 1.0 | 0.313 |
|  | 48 | 10.0 | 3.125 |
| 30 | 22 | 22.0 | 9.900 |
|  | 31 | 4.7 | 2.115 |
|  | 40 | 1.0 | 0.450 |
|  | 41 | 4.7 | 2.115 |
|  | 49 | 1.0 | 0.450 |

Fig. 13

HEAT UNITS USING A SOLID FUEL CAPABLE OF UNDERGOING AN EXOTHERMIC METAL OXIDATION-REDUCTION REACTION PROPAGATED WITHOUT AN IGNITER

RELATED APPLICATIONS

This application is a continuation of U.S. application Ser. No. 17/035,641, filed Sep. 28, 2020, now U.S. Pat. No. 11,484,668, entitled "Heat Units Using a Solid fuel Capable of Undergoing an Exothermic Metal Oxidation-Reduction Reaction Propagated without an Igniter", which is a continuation of U.S. application Ser. No. 15/712,468, filed Sep. 22, 2017, no U.S. Pat. No. 10,786,635, entitled "Heat Units Using a Solid fuel Capable of Undergoing an Exothermic Metal Oxidation-Reduction Reaction Propagated without an Igniter", which application is a continuation of U.S. application Ser. No. 13/217,385, filed Aug. 25, 2011, entitled "Heat Units Using a Solid Fuel Capable of Undergoing an Exothermic Metal Oxidation-Reduction Reaction Propagated without an Igniter", which application claims priority to U.S. Provisional Patent Application Ser. No. 61/377,377, filed Aug. 26, 2010, entitled "Heat Units Using a Solid Fuel Capable of Undergoing an Exothermic Metal Oxidation-Reduction Reaction Propagated without an Igniter", the entire disclosures of which are hereby incorporated by reference. Any disclaimer that may have occurred during the prosecution of the above-referenced applications is hereby expressly rescinded, and reconsideration of all relevant art is respectfully requested.

TECHNICAL FIELD

This disclosure is directed to heating units capable of rapid heating and to articles and methods employing such heating units, and more particularly to heating units using a solid fuel capable of undergoing an exothermic metal oxidation-reduction reaction propagated without an igniter.

BACKGROUND

Self-contained heating units using a solid fuel capable of undergoing an exothermic metal oxidation-reduction reaction are known. Such devices use a metal reducing agent and a metal containing oxidizing agent typically in combination with an additive such as a binder coated on the surface of an electively conductive substrate. Various embodiments of self-contained heating units utilizing such solid fuel layers are described in Hale, U.S. Patent Publication No. 2004/0234914, the entire disclosure of which is hereby incorporated by reference. The solid fuel capable of undergoing exothermic metal oxidation-reduction reaction has proven useful, in particular as part of a drug delivery device, because of the ability of the solid fuel to heat the substrate to several hundred degrees Celsius very rapidly, i.e., on the order of seconds and fractions of seconds. This rapid heating to a high temperature is useful for producing high purity aerosols of drugs coated on or in heat exchange relationship with the heat units. However, heat units using solid fuels capable of undergoing exothermic metal oxidation-reduction reaction have required actuation by one of a variety of ignition systems. Such ignition systems include, but are not limited to, resistive heating igniters, resistive heating with an arc, optical, percussive igniters. While each of these various starters have advantages and drawbacks with respect to other starter options, it would be advantageous if no starter or igniter was required to initiate the metal oxidation-reduction reaction Eliminating the igniter would minimize the components and manufacturing processing steps required to build heating units and dramatically reduce the cost while simultaneously increasing the safety and reliability of the heating units.

The present invention is directed toward overcoming one or more of the problems discussed above.

SUMMARY

A first aspect is a heating unit comprising an electrically conductive substrate. A solid fuel layer comprising a metal reducing agent, a metal containing oxidizing agent and a binder is coated on a surface of the substrate, the solid fuel layer having a solid fuel surface spaced from the substrate. A first electrode is coupled to the substrate. A second electrode is coupled to the solid fuel surface. A power supply is configured to be selectively coupled to the first and second electrodes to provide a voltage between the metallic substrate and the solid fuel surface. The voltage (and a small amount of current) acts to propagate an exothermic metal oxidation-reduction reaction without the use of an igniter.

Another aspect is a drug supply unit comprising an electrically conductive substrate having an exterior surface and an interior surface and a solid fuel layer comprising a metal reducing agent, a metal containing oxidizing agent and a binder coated on the interior surface of the substrate, with the solid fuel layer having a solid fuel surface spaced from the substrate. A first electrode is coupled to the substrate and a second electrode is coupled to the solid fuel surface. A power supply is configured to be selectively coupled to the first and the second electrodes to provide a voltage between the metallic substrate and the solid fuel surface to propagate an exothermic metal oxidation-reduction reaction within the enclosure. A drug is disposed on a portion of the exterior surface of the substrate.

A further aspect is an aerosol drug delivery device comprising a housing defining an airway and a heating unit as described above disposed within the airway. A drug is disposed on another surface of the substrate whereby upon coupling of the first and second electrodes to the battery the solid fuel is ignited to vaporize the drug.

Yet another aspect is a method of making a heating unit comprising coating a portion of the interior surface of a conductive substrate with a slurry of solid fuel comprising a metal reducing agent, a metal containing oxidizing agent and an inorganic binder. The slurry is solidified and a first electrode is coupled to the conductive substrate and a second electrode is coupled to a surface of the solid fuel.

It is to be understood that both the foregoing general description and the following detailed description are explanatory and are not restrictive of embodiments in the scope of the claims.

BRIEF DESCRIPTION OF THE DRAWINGS

FIG. 1 is a schematic elevation view of a first embodiment of a heating unit without an igniter comprising a fuel layer disposed on a surface of a substrate;

FIG. 2 is another embodiment of a heating unit without an igniter wherein the heat unit has an enclosure comprising a substrate with a solid fuel layer disposed on an interior surface of the substrate;

FIG. 3 is an embodiment of a heating unit without an igniter with a solid fuel layer sandwiched between two conductive substrates;

FIG. 4 is an embodiment of a heating unit without an igniter with a substrate having multiple discrete fuel layers selectively engaged by an electrode;

FIG. 13 is a chart of successfully actuated solid fuels of indicated thickness using capacitors of indicated voltages and capacitance applying the indicated energy.

DETAILED DESCRIPTION

Unless otherwise indicated, all numbers expressing quantities of ingredients, dimensions reaction conditions and so forth used in the specification and claims are to be understood as being modified in all instances by the term "about".

In this application and the claims, the use of the singular includes the plural unless specifically stated otherwise. In addition, use of "or" means "and/or" unless stated otherwise. Moreover, the use of the term "including", as well as other forms, such as "includes" and "included", is not limiting. Also, terms such as "element" or "component" encompass both elements and components comprising one unit and elements and components that comprise more than one unit unless specifically stated otherwise.

Figure 1:
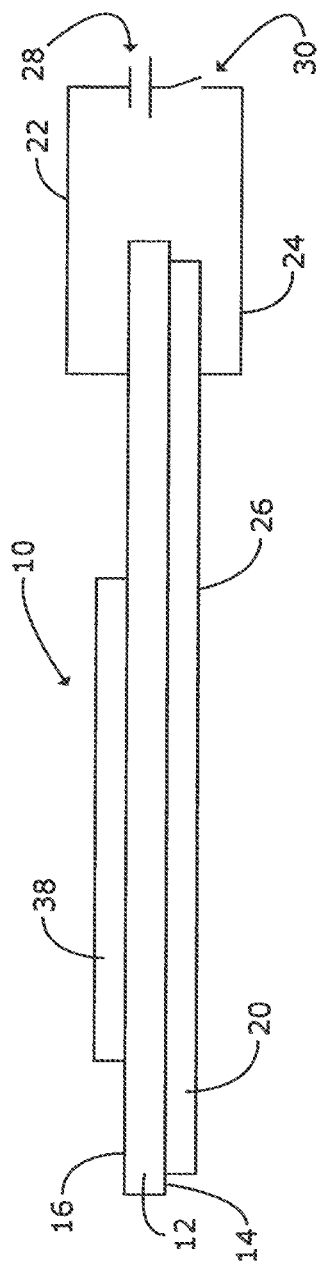
Figure 2:
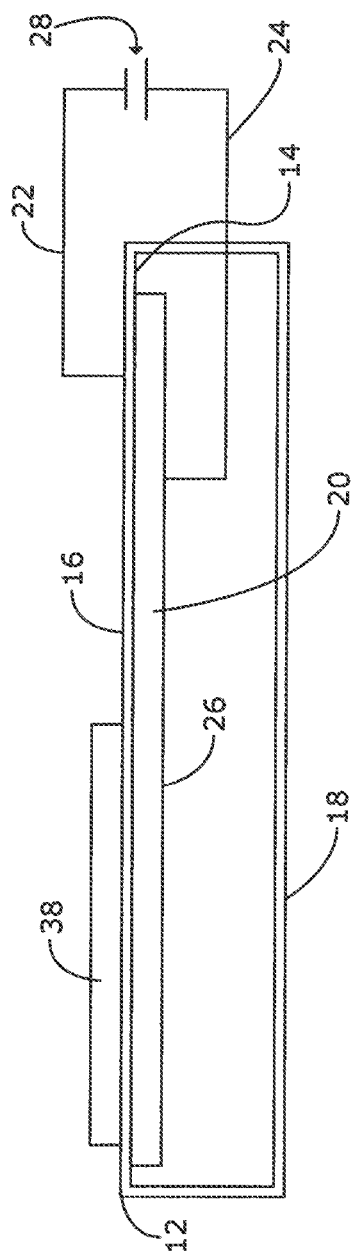

A basic embodiment of a heating unit 10 is depicted in FIG. 1. The heating unit 10 comprises an electrically conductive substrate 12 which can be formed from known electrically conductive materials, including, but not limited to, metals, such as aluminum, iron, copper, stainless steel and the like, as well as various alloys thereof. Some conductive ceramics and polymers may also be suitable substrate materials. A substrate can be formed of one or more of these materials and certain embodiments can have a multi-layer structure. For example, the substrate can comprise one or more films or coatings or multiple sheets or layers of material. A substrate can be of any appropriate geometry, including rectangular configurations illustrated herein. A substrate can have any suitable thickness. In certain embodiments, such as illustrated in FIG. 2, the substrate 12 may include an interior surface 14 and an exterior surface 16 and the substrate 12 can be incorporated into a sealed container 18 containing a solid fuel or reactant 20. In other embodiments (not shown) the solid fuel can be disposed on two adjacent areas of a surface of a substrate and the adjacent areas are folded over with an electrical lead therebetween. The edges of the substrate are then sealed together to form a two side reactant heat unit.

An article or object can be placed adjacent or in contact with the exterior surface 16 to receive conducted heat to achieve a desired action, such as forming or heating of a solid or fluid object, effecting a further reaction, or causing a phase change. For example, the conductive heat can effect a phase change on a compound in contact directly or indirectly with the exterior surface 16.

The components of the solid fuel can react in an exothermic reaction to produce heat. For example, the solid fuel can react in an exothermic oxidation-reduction reaction. An oxidation-reduction reaction refers to a chemical reaction in which one compound gains electrons and another compound loses electrons. The compound that gains electrons is referred to as an oxidizing agent, and the compound that loses electrons is referred to as a reducing agent. An example of an oxidation-reduction reaction is a chemical reaction of a compound with molecular oxygen ($O_2$) or an oxygen-containing compound that adds one or more oxygen atoms to the compound being oxidized. During the oxidation-reduction reaction, the molecular oxygen or the oxygen-containing compound is reduced by the compound being oxidized. The compound providing oxygen acts as the oxidizer or oxidizing agent. The compound being oxidized acts as the reducing agent. Oxidation-reduction reactions can be exothermic, meaning that the reactions generate heat. An example of an exothermic oxidation-reduction reaction is the thermite reaction of a metal with a metal oxidizing agent. In certain embodiments, a solid fuel can comprise a metal reducing agent and an oxidizing agent, such as for example, a metal-containing oxidizing agent.

In some embodiments, the metal reducing agent and the oxidizing agent can be in the form of a powder. The term "powder" refers to powders, particles, prills, flakes, and any other particulate that exhibits an appropriate size or surface area to sustain self-propagating ignition. For example, in some embodiments, the powder can comprise particles exhibiting an average diameter ranging from 0.1 µm to 200 µm.

In some embodiments, a metal reducing agent can include, but is not limited to molybdenum, magnesium, calcium, strontium, barium, boron, titanium, zirconium, vanadium, niobium, tantalum, chromium, tungsten, manganese, iron, cobalt, nickel, copper, zinc, cadmium, tin, antimony, bismuth, aluminum, and silicon. In certain embodiments, a metal reducing agent can include aluminum, zirconium, and titanium. In some embodiments, a metal reducing agent can comprise more than one metal reducing agent.

In some embodiments, an oxidizing agent can comprise oxygen, an oxygen based gas, or a solid oxidizing agent. In some embodiments, an oxidizing agent can comprise a metal-containing oxidizing agent. In some embodiments, a metal-containing oxidizing agent includes, but is not limited to, perchlorates and transition metal oxides. Perchlorates can include perchlorates of alkali metals or alkaline earth metals, such as, but not limited to, potassium perchlorate ($KClO_4$), potassium chlorate ($KClO_3$), lithium perchlorate ($LiClO_4$), sodium perchlorate ($NaClO_4$), and magnesium perchlorate [$Mg(ClO_4)_2$]. In some embodiments, transition metal oxides that function as oxidizing agents include, but are not limited to, oxides of molybdenum, such as $MoO_3$, iron, such as $Fe_2O_3$, vanadium ($V_2O_5$), chromium ($CrO_3$, $Cr_2O_3$), manganese ($MnO_2$), cobalt ($CO_3O_4$), silver ($Ag_2O$), copper (CuO), tungsten ($WO_3$), magnesium (MgO), and niobium ($Nb_2O_5$). In some embodiments, the metal-containing oxidizing agent can include more than one metal-containing oxidizing agent. Metal oxides having a melting point less than 1500° C. are believed suitable for the various embodiments disclosed herein.

In some embodiments, the metal reducing agent forming the solid fuel can be selected from zirconium, titanium and aluminum, and the metal-containing oxidizing agent can be selected from $MoO_3$ $MnO_2$ and $Fe_2O_3$.

In some embodiments, a solid fuel can comprise additive materials to facilitate, for example, binding of the metal containing oxidizing reagent and reducing agent in order to adhere the metal containing oxidizing agent and reducing agent to the substrate. The additive materials may also function as gelling agents, thixotropic agents or surfactants. Examples of binding materials include nitrocellulose, polyvinyl alcohol, diatomaceous earth, glass beads, colloidal silica, and a clay gelling agent.

In some embodiments, the binder is Laponite®, and in particular Laponite® RDS, as an inert additive material. Laponite® is a synthetic layered silicate, and in particular a magnesium phyllosilicate, with a structure resembling that of the natural clay mineral hectorite ($Na_{0.4}Mg_{2.7}Li_{0.3}Si_4O_{10}(OH)_2$). Laponite® RD is a commercial grade material which, when added to water, rapidly disperses to form a gel when hydrated (Southern Clay Products, Gonzales, Tex.). Laponite® RD has the following chemical analysis in weight percent: 59.5% $SiO_2$: 27.5% MgO: 0.8% $Li_2O$: 2.8% $Na_2O$. Laponite® RDS (Southern Clay Products, Gonzales, TX) is a commercially available sol-forming grade of Laponite® modified with a polyphosphate dispersing agent, or peptizer, to delay rheological activity until the Laponite® RDS is added as a dispersion into a formulation. A sol refers to a colloid having a continuous liquid phase in which solid is suspended in a liquid. Laponite® RDS has the following chemical analysis in weight percent: 54.5% $SiO_2$: 26% MgO: 0.8% $Li_2O$: 5.6% $Na_2O$: 4.1% $P_2O_5$. In the presence of electrolytes, Laponites® can act as gelling and thixotropic agents. Thixotropy refers to the property of a material to exhibit decreased viscosity under shear.

When incorporated into a solid fuel composition comprising a metal reducing agent and a metal-containing oxidizing agent, such as any of those disclosed herein, in addition to imparting gelling and thixotropic properties, Laponite® RDS can also act as binder. A binder refers to an additive that produces bonding strength in a final product. The binder can impart bonding strength, for example, by forming a bridge, film, matrix, or chemically self-react or react with other constituents of the formulation.

The binder may include other inorganic silicate based binders in addition to Laponite®.

The solid fuel layer is formed into a slurry by combining the metal reducing agent, metal containing oxidizing agent and binder and may be applied to a substrate by tip dispensing, spraying, screen printing or Meyer bar coding. The solid fuel layer is typically applied as a single coat and dried at an elevated temperature of between 40-200° C., as appropriate.

In some embodiments, for example, when the solid fuel is disposed on a substrate as a film or thin layer, wherein the thickness of the thin layer of solid fuel can range from 20 μm to 6000 μm, it can be useful that the solid fuel adhere to the surface of the substrate and that the constituents of the solid fuel adhere to each other, and maintain physical integrity. In some embodiments, it can be useful that the solid fuel remain adhered to the substrate surface and maintain physical integrity during processing, storage, and use during which time the solid fuel coating can be exposed to a variety of mechanical and environmental conditions. Several additives, such as those disclosed herein, can be incorporated into the solid fuel to impart adhesion and physical robustness to the solid fuel coating.

Other useful additive materials include glass beads, diatomaceous earth, nitrocellulose, polyvinyl alcohol, and other polymers that may function as binders. In certain embodiments, the solid fuel can comprise more than one additive material. The components of the solid fuel comprising the metal, oxidizing agent or additive material or any appropriate aqueous- or organic-soluble binder, can be mixed by any appropriate physical or mechanical method to achieve a useful level of dispersion or homogeneity. In some embodiments, the solid fuel can be degas sed.

In some embodiments, the solid fuel layer comprises by weight 10-90% zirconium, 10-90% metal containing oxidizing agent and 1-15% binder, such as Laponite®. In other embodiments the solid fuel layer comprises by weight 40-70% zirconium, 10-40% metallic oxidizing agent and 3-10% binder.

In some embodiments, a solid fuel can be machined, molded, pre-formed or packed. The solid fuel can be formed as a separate element configured to be inserted into a heating unit, or the solid fuel can be applied directly to a heating unit. In some embodiments, a solid fuel can be coated, applied, or deposited directly onto a substrate forming part of a heating unit, onto a support that can be incorporated into a heating unit, or onto a support configured to transfer the solid fuel to a substrate forming a heating unit.

Referring to FIG. 1, a first electrode 22 is coupled to the substrate 12 and a second electrode 24 is coupled to a solid fuel surface 26 of the solid fuel layer 20 without an igniter or starter. The electrodes 22, 24 are in turn coupled to opposite leads of a power supply 28. A voltage can be selectively applied between the substrate 16 and the solid fuel surface 26 by selective closing of the switch 30.

Application of a voltage across certain solid fuel layer compositions is surprisingly found to propagate a sustaining exothermic metal oxidation-reduction reaction in the solid fuel layer 20 without an igniter or starter. Once a portion of the solid fuel layer is ignited, the heat generated by the oxidation-reduction reaction ignites adjacent unburned fuel until all the fuel is consumed in the process of the chemical reaction. Without being bound by theory, we can postulate that the metal oxide, the metal reducing agent or the binder may possess capacitive properties such that upon application of the voltage to the conductive substrate and the solid fuel layer, electrical energy is stored in the capacitive material until the buildup of potential (or voltage) results in electrical arcing occurring on a nanoscale between gaps in particles in the solid fuel coating. This arcing initiates an oxidation of air in the nanoscale gap creating enough heat to propagate the metal oxidation-reduction reaction.

The voltage and current necessary to propagate the reaction appear to be minimal. For example, a 9-volt battery has been used as the power supply and has successfully propagated the oxidation-reduction reaction. Other possible power supplies include conductive film coupled to a capacitor, a thin film battery and a lithium battery.

FIG. 3 is another embodiment of a heating unit wherein the solid fuel layer 20 is sandwiched between a pair of electrically conductive substrates 12. The electrically conductive substrates 12 are otherwise electrically insulated from one another. The first electrode 22 is coupled to a substrate and the second electrode 24 is coupled to the other substrate 12. In the same manner described above, application of the voltage across the substrates induces the self sustained metal oxidation-reduction reaction.

FIG. 4 is another embodiment showing a plurality of solid fuel layers 20 disposed on a substrate 12. In this embodiment the first electrode 22 is coupled to the substrate 12 and the second electrode 24 is selectively coupled to discrete solid fuel layers 20 so that upon application of a voltage across the solid fuel layers 20 the metal oxidation-reduction reaction is propagated by closing the switch 30. Selective coupling of the second electrode 24 to the various solid fuel layers 20 is illustrated by ghost lines in FIG. 4.

Some embodiments may include a drug supply unit comprising the heating unit described above. The drug supply unit can be used in a drug delivery device where a drug is to be thermally vaporized and then condensed for administration to a user. In some embodiments, the drug condensate can be administered by inhalation, nasal ingestion or topically. "Drug" refers to any compound for therapeutic use or non-therapeutic use, including therapeutic agents or substances. "Therapeutic agent" refers to any compound for use in the diagnosis, cure, mitigation, treatment or prevention of disease, and any compound used in the mitigation or treatment of symptoms of disease. "Non-therapeutic agent," on the other hand, refers to compounds used for non-therapeutic use, typically for a recreational or experimental purpose. Referring to FIG. 1, the heating unit is converted to a drug supply unit by providing a film of a drug 38 on an exterior surface 16 of the substrate 12.

In some embodiments, the film 38 can be applied to exterior substrate surface 16 by any appropriate method and can depend at least in part on the physical properties of the drug and the final thickness of the film. In certain embodiments, methods of applying a drug to the exterior substrate surface include, but are not limited to, brushing, dip coating, spray coating, screen printing, roller coating, inkjet printing, vapor-phase deposition, spin coating, and the like. In some embodiments, the drug can be prepared as a solution comprising at least one solvent and applied to the exterior surface. In some embodiments, a solvent can comprise a volatile solvent such as, for example, but not limitation, acetone or isopropanol. In some embodiments, the drug can be applied to the exterior surface of the substrate as a melt. In some embodiments, the drug can be applied to a support having a release coating and transferred to a substrate from the support. For drugs that are liquid at room temperature, thickening agents can be admixed with the drug to produce a viscous composition comprising the drug that can be applied to the exterior substrate surface by any appropriate method, including those described herein. In some embodiments, a film of compound can be formed during a single application or can be formed during repeated applications to increase the final thickness of the film. In some embodiments, the final thickness of a film of drug disposed on the exterior substrate surface can be less than 60 µm, in some embodiments less than 20 µm and in some embodiments less than 10 µm, in some embodiments the film thickness can range from 0.02 µm to 20 µm, and in some embodiments can range from 0.1 µm to 10 µm.

In some embodiments, the film can comprise a therapeutically effective amount of at least one drug. Therapeutically effective amount refers to an amount sufficient to affect treatment when administered to a patient or user in need of treatment. Treating or treatment of any disease, condition, or disorder refers to arresting or ameliorating a disease, condition or disorder, reducing the risk of acquiring a disease, condition or disorder, reducing the development of a disease, condition or disorder or at least one of the clinical symptoms of the disease, condition or disorder, or reducing the risk of developing a disease, condition or disorder or at least one of the clinical symptoms of a disease or disorder. Treating or treatment also refers to inhibiting the disease, condition or disorder, either physically, e.g. stabilization of a discernible symptom, physiologically, e.g., stabilization of a physical parameter, or both, and inhibiting at least one physical parameter that may not be discernible to the patient. Further, treating or treatment refers to delaying the onset of the disease, condition or disorder or at least symptoms thereof in a patient which may be exposed to or predisposed to a disease, condition or disorder even though that patient does not yet experience or display symptoms of the disease, condition or disorder. In some embodiments, the drug film can comprise one or more pharmaceutically acceptable carriers, adjuvants, or excipients. Pharmaceutically acceptable refers to approved or approvable by a regulatory agency of the Federal or a state government or listed in the U.S. Pharmacopoeia or other generally recognized pharmacopoeia for use in animals, and more particularly in humans.

The drug supply unit is configured such that the solid fuel heats a portion of the exterior surface of the substrate to a temperature sufficient to thermally vaporize the drug in certain embodiments within at least 3 seconds following ignition of the solid fuel, in other embodiments within 1 second following ignition of the solid fuel, in other embodiments within 800 milliseconds following ignition of the solid fuel, in other embodiments within 500 milliseconds following ignition of the solid fuel, and in other embodiments within 250 milliseconds following ignition of the solid fuel.

In some embodiments, a drug supply unit can generate an aerosol comprising a drug that can be inhaled directly by a user or can be mixed with a delivery vehicle, such as a gas, to produce a stream for delivery, e.g., via a spray nozzle, to a topical site for a variety of treatment regimens, including acute or chronic treatment of a skin condition, administration of a drug to an incision site during surgery, or to an open wound.

In some embodiments, rapid vaporization of a drug film can occur with minimal thermal decomposition of the drug. For example, in some embodiments, less than 10% of the drug is decomposed during thermal vaporization, and in some embodiments, less than 5% of the drug is decomposed during thermal vaporization. In some embodiments, a drug can undergo a phase transition to a liquid state and then to a gaseous state, or can sublime, i.e., pass directly from a solid state to a gaseous state. In some embodiments, a drug can include a pharmaceutical compound. In some embodiments, the drug can comprise a therapeutic compound or a non-therapeutic compound. Classes of drugs that can be used include, but are not limited to, anesthetics, anticonvulsants, antidepressants, antidiabetic agents, antidotes, antiemetics, antihistamines, anti-infective agents, antineoplastics, antiparkisonian drugs, antirheumatic agents, antipsychotics, anxiolytics, appetite stimulants and suppressants, blood modifiers, cardiovascular agents, central nervous system stimulants, drugs for Alzheimer's disease management, drugs for cystic fibrosis management, diagnostics, dietary supplements, drugs for erectile dysfunction, gastrointestinal agents, hormones, drugs for the treatment of alcoholism, drugs for the treatment of addiction, immunosuppressives, mast cell stabilizers, migraine preparations, motion sickness products, drugs for multiple sclerosis management, muscle relaxants, nonsteroidal anti-inflammatories, opioids, other analgesics and stimulants, opthalmic preparations, osteoporosis preparations, prostaglandins, respiratory agents, sedatives and hypnotics, skin and mucous membrane agents, smoking cessation aids, Tourette's syndrome agents, urinary tract agents, and vertigo agents.

Examples of anesthetic include ketamine and lidocaine.

Examples of anticonvulsants include compounds from one of the following classes: GABA analogs, tiagabine, vigabatrin; barbiturates such as pentobarbital; benzodiazepines such as clonazepam; hydantoins such as phenyloin;

phenyltriazines such as lamotrigine; miscellaneous anticonvulsants such as carbamazepine, topiramate, valproic acid, and zonisamide.

Examples of antidepressants include amitriptyline, amoxapine, benmoxine, butriptyline, clomipramine, desipramine, dosulepin, doxepin, imipramine, kitanserin, lofepramine, medifoxamine, mianserin, maprotoline, mirtazapine, nortriptyline, protriptyline, trimipramine, venlafaxine, viloxazine, citalopram, cotinine, duloxetine, fluoxetine, fluvoxamine, milnacipran, nisoxetine, paroxetine, reboxetine, sertraline, tianeptine, acetaphenazine, binedaline, brofaromine, cericlamine, clovoxamine, iproniazid, isocarboxazid, moclobemide, phenyhydrazine, phenelzine, selegiline, sibutramine, tranylcypromine, ademetionine, adrafinil, amesergide, amisulpride, amperozide, benactyzine, bupropion, caroxazone, gepirone, idazoxan, metralindole, milnacipran, minaprine, nefazodone, nomifensine, ritanserin, roxindole, S-adenosylmethionine, escitalopram, tofenacin, trazodone, tryptophan, and zalospirone.

Examples of antidiabetic agents include pioglitazone, rosiglitazone, and troglitazone.

Examples of antidotes include edrophonium chloride, flumazenil, deferoxamine, nalmefene, naloxone, and naltrexone.

Examples of antiemetics include alizapride, azasetron, benzquinamide, bromopride, buclizine, chlorpromazine, cinnarizine, clebopride, cyclizine, diphenhydramine, diphenidol, dolasetron, droperidol, granisetron, hyoscine, lorazepam, dronabinol, metoclopramide, metopimazine, ondansetron, perphenazine, promethazine, prochlorperazine, scopolamine, triethylperazine, trifluoperazine, triflupromazine, trimethobenzamide, tropisetron, domperidone, and palonosetron.

Examples of antihistamines include astemizole, azatadine, brompheniramine, carbinoxamine, cetrizine, chlorpheniramine, cinnarizine, clemastine, cyproheptadine, dexmedetomidine, diphenhydramine, doxylamine, fexofenadine, hydroxyzine, loratidine, promethazine, pyrilamine and terfenidine.

Examples of anti-infective agent include compounds selected from one of the following classes: antivirals such as efavirenz; AIDS adjunct agents such as dapsone; aminoglycosides such as tobramycin; antifungals such as fluconazole; antimalarial agents such as quinine; antituberculosis agents such as ethambutol; β-lactams such as cefinetazole, cefazolin, cephalexin, cefoperazone, cefoxitin, cephacetrile, cephaloglycin, cephaloridine; cephalosporins, such as cephalosporin C, cephalothin; cephamycins such as cephamycin A, cephamycin B, and cephamycin C, cephapirin, cephradine; leprostatics such as clofazimine; penicillins such as ampicillin, amoxicillin, hetacillin, carfecillin, carindacillin, carbenicillin, amylpenicillin, Azidocillin, benzylpenicillin, clometocillin, cloxacillin, cyclacillin, methicillin, nafcillin, 2-pentenylpenicillin, penicillin N, penicillin O, penicillin S, penicillin V, dicloxacillin; diphenicillin; heptylpenicillin; and metampicillin; quinolones such as ciprofloxacin, clinafloxacin, difloxacin, grepafloxacin, norfloxacin, ofloxacine, temafloxacin; tetracyclines such as doxycycline and oxytetracycline; miscellaneous anti-infectives such as linezolide, trimethoprim and sulfamethoxazole.

Examples of anti-neoplastic agents include droloxifene, tamoxifen, and toremifene.

Examples of antiparkisonian drugs include amantadine, baclofen, biperiden, benztropine, orphenadrine, procyclidine, trihexyphenidyl, levodopa, carbidopa, andropinirole, apomorphine, benserazide, bromocriptine, budipine, cabergoline, eliprodil, eptastigmine, ergoline, galanthamine, lazabemide, lisuride, mazindol, memantine, mofegiline, pergolide, piribedil, pramipexole, propentofylline, rasagiline, remacemide, ropinerole, selegiline, spheramine, terguride, entacapone, and tolcapone.

Examples of antirheumatic agents include diclofenac, hydroxychloroquine and methotrexate.

Examples of antipsychotics include acetophenazine, alizapride, amisulpride, amoxapine, amperozide, aripiprazole, benperidol, benzquinamide, bromperidol, buramate, butaclamol, butaperazine, carphenazine, carpipramine, chlorpromazine, chlorprothixene, clocapramine, clomacran, clopenthixol, clospirazine, clothiapine, clozapine, cyamemazine, droperidol, flupenthixol, fluphenazine, fluspirilene, haloperidol, loxapine, melperone, mesoridazine, metofenazate, molindrone, olanzapine, penfluridol, pericyazine, perphenazine, pimozide, pipamerone, piperacetazine, pipotiazine, prochlorperazine, promazine, quetiapine, remoxipride, risperidone, sertindole, spiperone, sulpiride, thioridazine, thiothixene, trifluperidol, triflupromazine, trifluoperazine, ziprasidone, zotepine, and zuclopenthixol.

Examples of anxiolytics include alprazolam, bromazepam, oxazepam, buspirone, hydroxyzine, mecloqualone, medetomidine, metomidate, adinazolam, chlordiazepoxide, clobenzepam, flurazepam, lorazepam, loprazolam, midazolam, alpidem, alseroxlon, amphenidone, azacyclonol, bromisovalum, captodiamine, capuride, carbcloral, carbromal, chloral betaine, enciprazine, flesinoxan, ipsapiraone, lesopitron, loxapine, methaqualone, methprylon, propanolol, tandospirone, trazadone, zopiclone, and zolpidem.

An example of an appetite stimulant is dronabinol.

Examples of appetite suppressants include fenfluramine, phentermine and sibutramine.

Examples of blood modifiers include cilostazol and dipyridamol.

Examples of cardiovascular agents include benazepril, captopril, enalapril, quinapril, ramipril, doxazosin, prazosin, clonidine, labetolol, candesartan, irbesartan, losartan, telmisartan, valsartan, disopyramide, flecanide, mexiletine, procainamide, propafenone, quinidine, tocainide, amiodarone, dofetilide, ibutilide, adenosine, gemfibrozil, lovastatin, acebutalol, atenolol, bisoprolol, esmolol, metoprolol, nadolol, pindolol, propranolol, sotalol, diltiazem, nifedipine, verapamil, spironolactone, bumetanide, ethacrynic acid, furosemide, torsemide, amiloride, triamterene, and metolazone.

Examples of central nervous system stimulants include amphetamine, brucine, caffeine, dexfenfluramine, dextroamphetamine, ephedrine, fenfluramine, mazindol, methylphenidate, pemoline, phentermine, sibutramine, and modafinil.

Examples of drugs for Alzheimer's disease management include donepezil, galanthamine and tacrin.

Examples of drugs for cystic fibrosis management include CPX (ciprofloxacin), IBMX (3-isobutyl-1-methylxanthine), XAC and analogues; 4-phenylbutyric acid; genistein and analogous isoflavones; and milrinone.

Examples of diagnostic agents include adenosine and aminohippuric acid.

Examples of dietary supplements include melatonin and vitamin-E.

Examples of drugs for erectile dysfunction include tadalafil, sildenafil, vardenafil, apomorphine, apomorphine diacetate, phentolamine, and yohimbine.

Examples of gastrointestinal agents include loperamide, atropine, hyoscyamine, famotidine, lansoprazole, omeprazole, and rebeprazole.

Examples of hormones include: testosterone, estradiol, and cortisone.

Examples of drugs for the treatment of alcoholism include naloxone, naltrexone, and disulfiram.

Examples of drugs for the treatment of addiction it is buprenorphine.

Examples of immunosupressives includemycophenolic acid, cyclosporin, azathioprine, tacrolimus, and rapamycin.

Examples of mast cell stabilizers include cromolyn, pemirolast, and nedocromil.

Examples of drugs for migraine headache include almotriptan, alperopride, codeine, dihydroergotamine, ergotamine, eletriptan, frovatriptan, isometheptene, lidocaine, lisuride, metoclopramide, naratriptan, oxycodone, propoxyphene, rizatriptan, sumatriptan, tolfenamic acid, zolmitriptan, amitriptyline, atenolol, clonidine, cyproheptadine, diltiazem, doxepin, fluoxetine, lisinopril, methysergide, metoprolol, nadolol, nortriptyline, paroxetine, pizotifen, pizotyline, propanolol, protriptyline, sertraline, timolol, and verapamil.

Examples of motion sickness products include diphenhydramine, promethazine, and scopolamine.

Examples of drugs for multiple sclerosis management include bencyclane, methylprednisolone, mitoxantrone, and prednisolone.

Examples of muscle relaxants include baclofen, chlorzoxazone, cyclobenzaprine, methocarbamol, orphenadrine, quinine, and tizanidine.

Examples of nonsteroidal anti-inflammatory drugs include aceclofenac, acetaminophen, alminoprofen, amfenac, aminopropylon, amixetrine, aspirin, benoxaprofen, bromfenac, bufexamac, carprofen, celecoxib, choline, salicylate, cinchophen, cinmetacin, clopriac, clometacin, diclofenac, diflunisal, etodolac, fenoprofen, flurbiprofen, ibuprofen, indomethacin, indoprofen, ketoprofen, ketorolac, mazipredone, meclofenamate, nabumetone, naproxen, parecoxib, piroxicam, pirprofen, rofecoxib, sulindac, tolfenamate, tolmetin, and valdecoxib.

Examples of opioid drugs include alfentanil, allylprodine, alphaprodine, anileridine, benzylmorphine, bezitramide, buprenorphine, butorphanol, carbiphene, cipramadol, clonitazene, codeine, dextromoramide, dextropropoxyphene, diamorphine, dihydrocodeine, diphenoxylate, dipipanone, fentanyl, hydromorphone, L-alpha acetyl methadol, lofentanil, levorphanol, meperidine, methadone, meptazinol, metopon, morphine, nalbuphine, nalorphine, oxycodone, papaveretum, pethidine, pentazocine, phenazocine, remifentanil, sufentanil, and tramadol.

Examples of other analgesic drugs include apazone, benzpiperylon, benzydramine, caffeine, clonixin, ethoheptazine, flupirtine, nefopam, orphenadrine, propacetamol, and propoxyphene.

Examples of opthalmic preparation drugs include ketotifen and betaxolol.

Examples of osteoporosis preparation drugs alendronate, estradiol, estropitate, risedronate and raloxifene.

Examples of prostaglandin drugs include epoprostanol, dinoprostone, misoprostol, and alprostadil.

Examples of respiratory agents include albuterol, ephedrine, epinephrine, fomoterol, metaproterenol, terbutaline, budesonide, ciclesonide, dexamethasone, flunisolide, fluticasone propionate, triamcinolone acetonide, ipratropium bromide, pseudoephedrine, theophylline, montelukast, zafirlukast, ambrisentan, bosentan, enrasentan, sitaxsentan, tezosentan, iloprost, treprostinil, and pirfenidone.

Examples of sedative and hypnotic drugs include butalbital, chlordiazepoxide, diazepam, estazolam, flunitrazepam, flurazepam, lorazepam, midazolam, temazepam, triazolam, zaleplon, zolpidem, and zopiclone.

Examples of skin and mucous membrane agents include isotretinoin, bergapten and methoxsalen.

Examples of smoking cessation aids include nicotine and varenicline.

An example of a Tourette's syndrome agent includes pimozide.

Examples of urinary tract agents include tolteridine, darifenicin, propantheline bromide, and oxybutynin.

Examples of vertigo agents include betahistine, indolizine and meclizine.

In certain embodiments, a drug can further comprise substances to enhance, modulate or control release, aerosol formation, intrapulmonary delivery, therapeutic efficacy, therapeutic potency, stability, and the like. For example, to enhance therapeutic efficacy a drug can be co-administered with one or more active agents to increase the absorption or diffusion of the first drug through the pulmonary alveoli, or to inhibit degradation of the drug in the systemic circulation. In certain embodiments, a drug can be co-administered with active agents having pharmacological effects that enhance the therapeutic efficacy of the drug. In certain embodiments, a drug can comprise compounds that can be used in the treatment of one or more diseases, conditions, or disorders. In certain embodiments, a drug can comprise more than one compound for treating one disease, condition, or disorder, or for treating more than one disease, condition, or disorder.

The embodiment of FIG. 4 has multiple solid fuel layers 20 suitable for a multidose drug supply unit by application of discrete layers of drugs 38 opposite the solid fuel layers 20. By selectively applying the electrode 24 to the solid fuel layers 20, corresponding discrete drug layers 38 can be vaporized.

Figure 5:
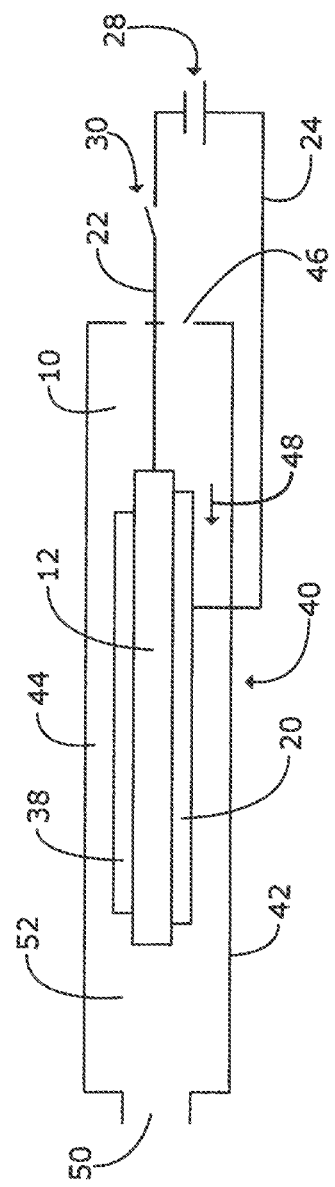
FIG. 5 is a schematic representation of a drug delivery device utilizing a heating unit of FIG. 1.

FIG. 5 is a schematic representation of a drug delivery device 40. The drug delivery device 40 can be used in combination with any of the drug supply units illustrated in FIGS. 1-4 or described herein. The drug delivery device 40 comprises a housing 42 surrounding a drug supply unit 10 and the housing 42 defines an airway 44. In use, air can be drawn through the housing 42 via the airway 44 by drawing air in through the inlet 46 in the direction of the arrow 48 to the outlet 50. In use, a drug layer 38 is vaporized and the vaporized drug is entrained in the air and then condenses to form an aerosol in the condensation space 52 so that a condensation aerosol can be delivered through the outlet 50. As described in the '914 publication, the drug delivery device can be configured and dimensioned to provide required airflow rates for forming aerosol particles of select size from various drugs.

EXAMPLES AND DATA

Below a number of examples of formulations and variations in parameters used in building and testing heating units in accordance with the disclosure herein are set forth. Variation of at least the following parameters have been found to effect the energy requirements necessary to initiate the metal oxidation-reduction reaction:

1. Adjustment of the formulation of the solid fuel;
2. Varying the thickness of the solid fuel coating;
3. Pressure of contact between the solid fuel and an electrode;
4. Pulse duration of energy delivery;
5. Resistance of the formulation;
6. Voltage applied between the surface of the solid fuel and the conductive substrate; and
7. Where the energy source is a capacitor, the capacitance of the capacitor.

Figure 6:
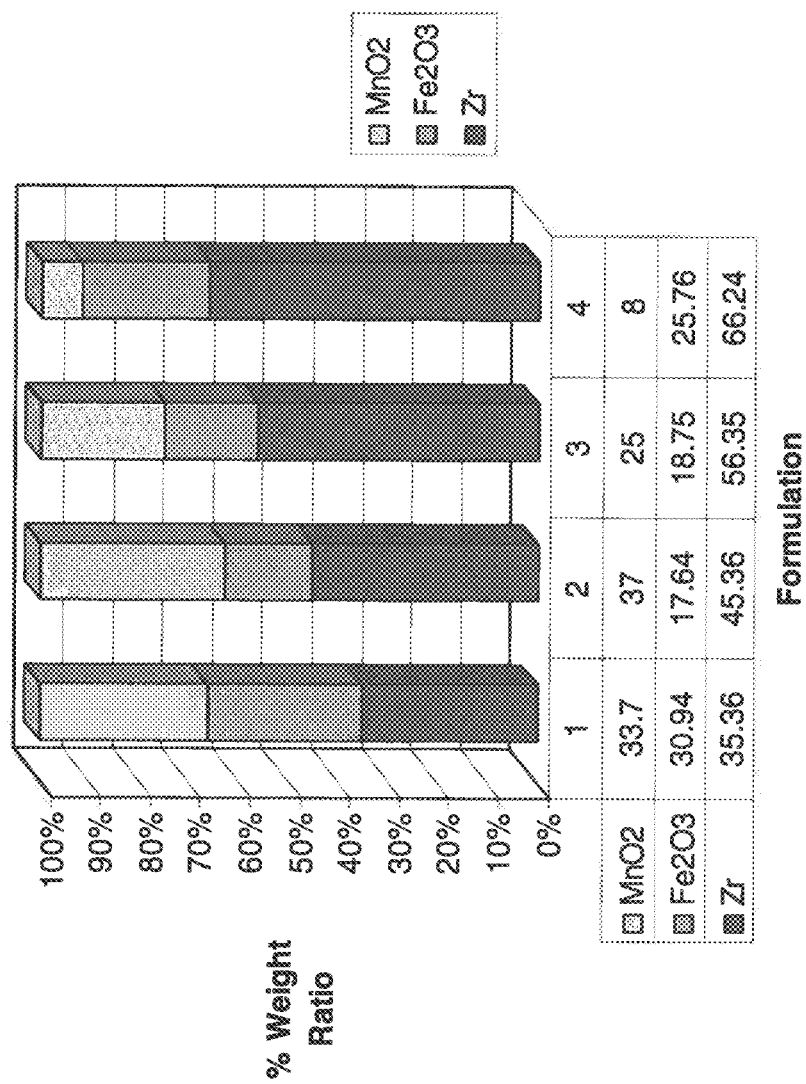
FIG. 6 is a bar graph illustrating various formulations of solid fuel.
Figure 7:
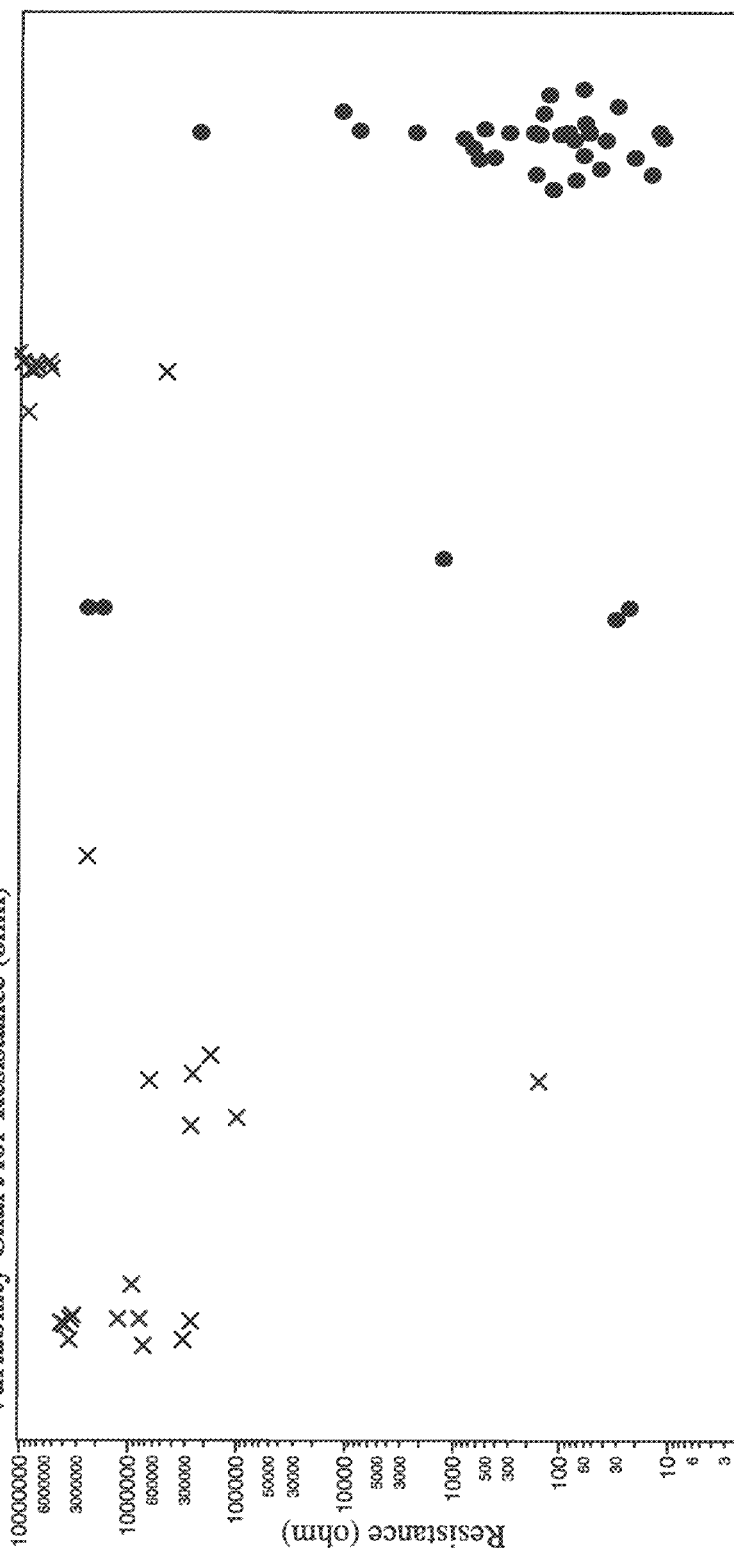
FIG. 7 is a chart indicating variability of resistance of the formulations of FIG. 6 that did or did not activate.

Four different solid fuel formulations were made using the indicated relative weight percentages of manganese ($MnO_2$), ferric oxide ($Fe_2O_3$) and zirconium (Zr) set forth in FIG. 6. In addition, essentially the same weight percentage of Laponite® formulation (in a range of 2-10% of the total weight) was part of the formulations, though it is not indicated in FIG. 6. The various solid fuel formulations were then connected to a power supply comprising a 10 volt, 1000 microfarad capacitor. FIG. 7 demonstrates which formulations were actuated by the power supply and the measured resistance of the solid fuel.

Other formulations of metal oxides and metal reducing agent that could be activated by application of a voltage included copper oxide ($Cu_2O$) and zirconium; copper (II) oxide (CuO) and zirconium; molybdenum trioxide ($MoO_3$) and zirconium; ferric oxide ($Fe_2O_3$) and zirconium; ferric oxide ($Fe_2O_3$), manganese dioxide ($MnO_2$) and zirconium; and ferric oxide ($Fe_2O_3$), manganese dioxide ($MnO_2$), plus nano carbon particles. Formulations that failed to activate included zinc oxide (ZnO) and zirconium (presumably because ZnO has a high melting point), a pure Zr coating and a pure Ti coating.

Figure 8:
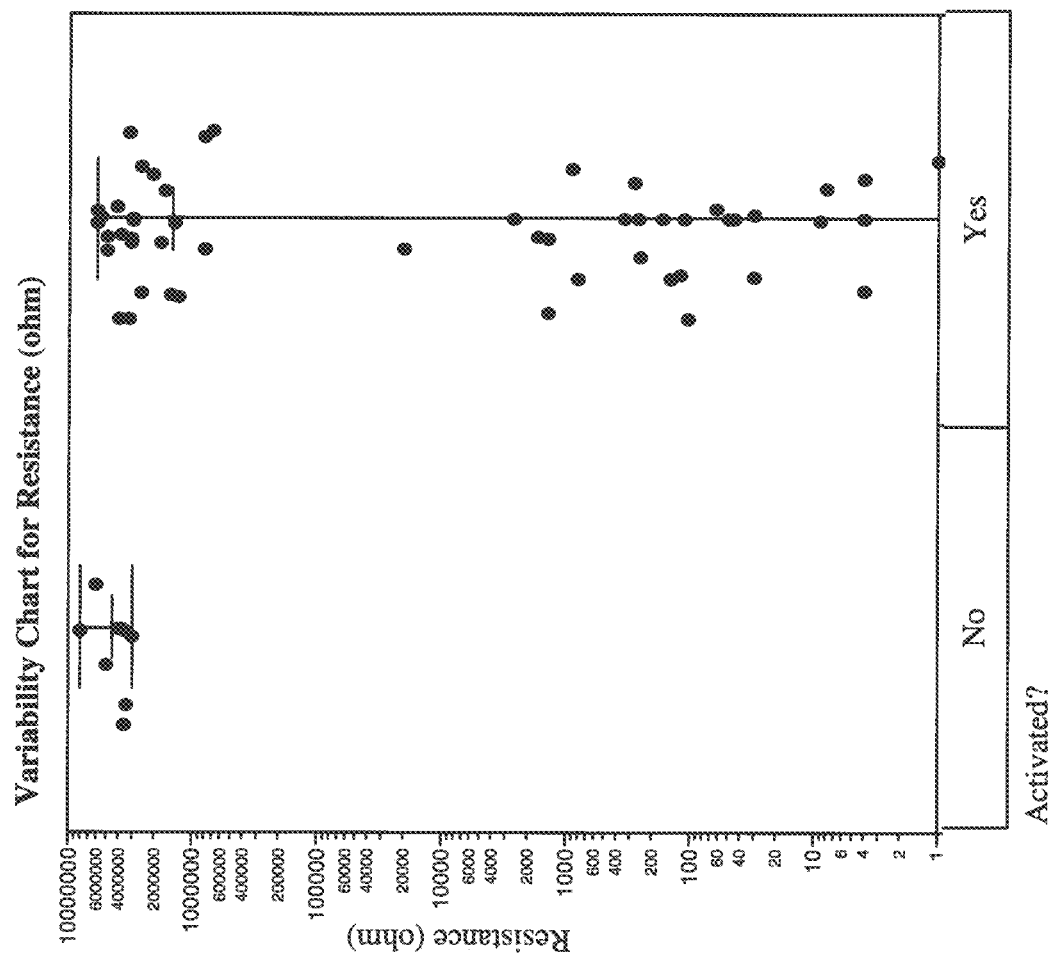
FIG. 8 is a chart further illustrating variability of resistance of select formulations of solid fuels that did or did not activate.

Tests showed that reliability of the solid fuel ignition by application of a 10 v, 1000 µF capacitor improved markedly when the solid fuel resistance was lower than one million ohms. This is demonstrated by the data charted in FIG. 8.

Figure 9:
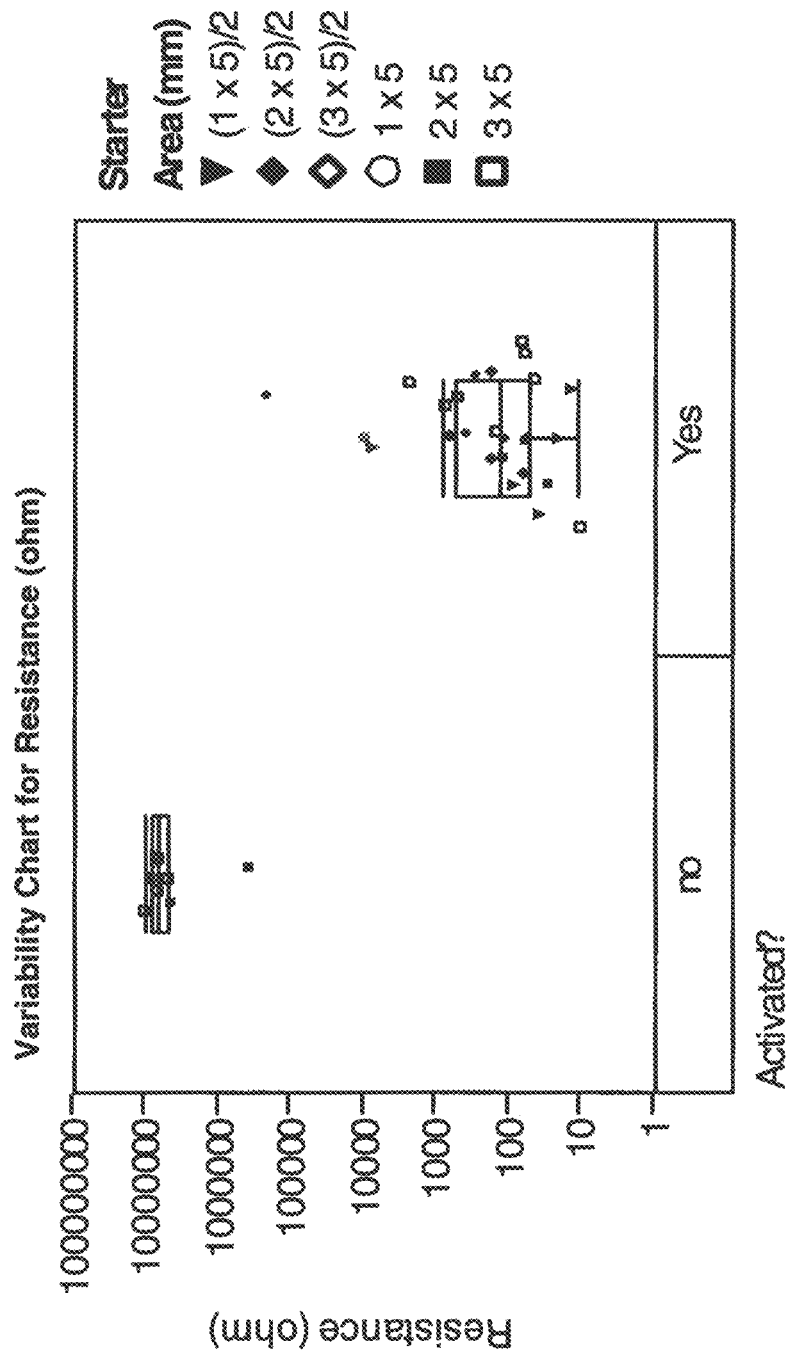
FIG. 9 is a chart illustrating the effect of surface area of a solid fuel layer on resistance.

Varying the starter area did not appear to improve resistance. This is illustrated by the data plotted in FIG. 9.

Data collected investigating the effectiveness of the reactive coating interestingly showed that to a point, increasing reactant thickness initially lowered the voltage required for activation. In this example the reactant contained the following relative dry weight percentage ratios of Zr, $Fe_2O_3$ and $MnO_2$:

$ZR_{AB}$—66.24%
$Fe_2O_3$—25.76%
$MnO_2$—8%

Figure 10:
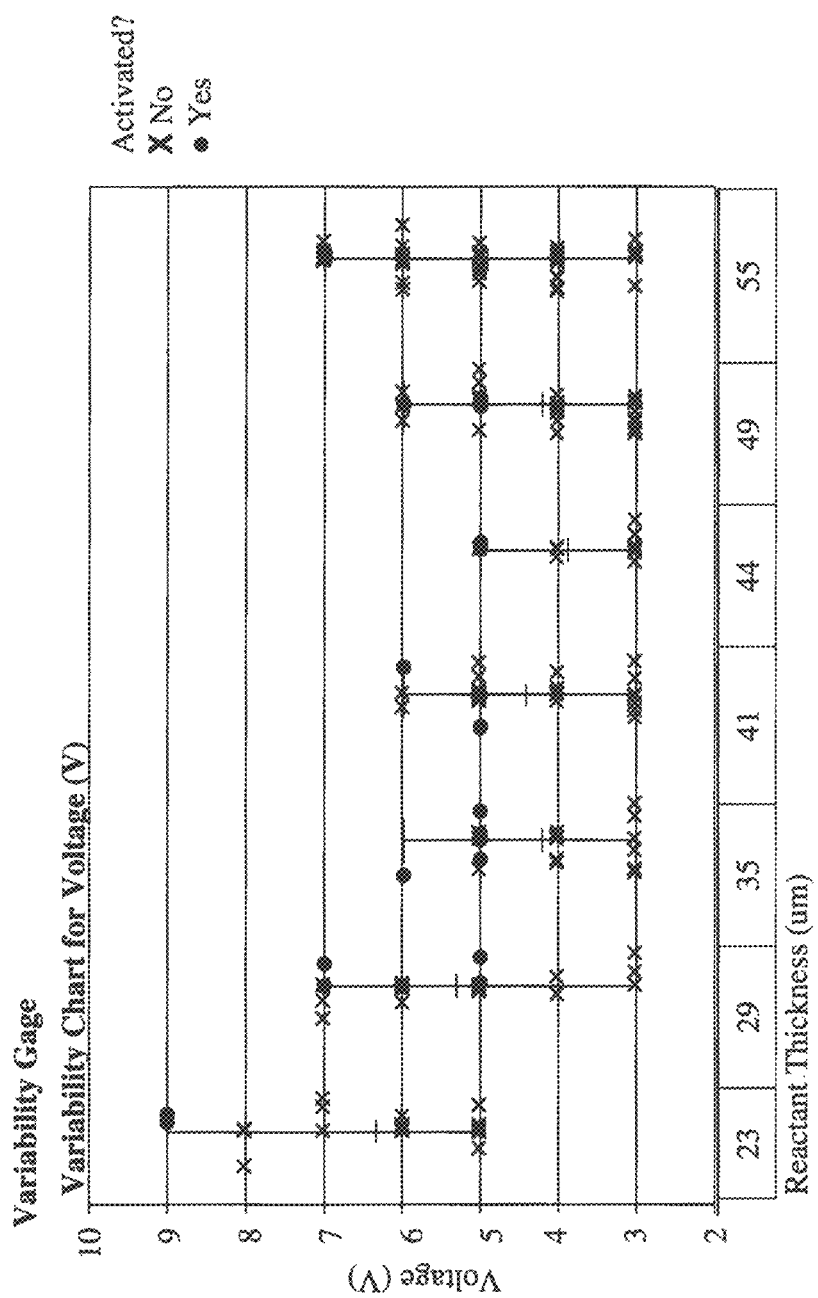
FIG. 10 is a chart illustrating activation of varying solid fuel thickness with different applied voltages.

In addition, as with other examples, the formula included 2-10% by weight Laponite® based on the total weight of the formulation. FIG. 10 shows, surprisingly, that as the thickness of the solid fuel increased, activation of the solid fuel required a lower voltage. The indicated voltage was provided by a power supply delivered for 50 µs.

Figure 11A:
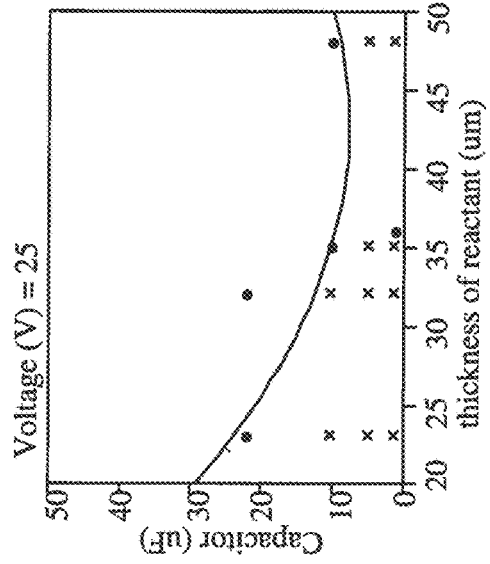
FIGS. 11A-11C are graphs of activated solid fuels showing capacitance versus solid fuel thickness at various voltages.
Figure 11B:
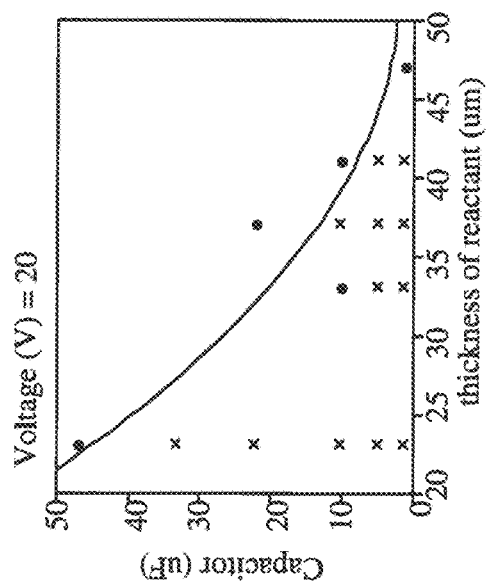
Figure 11C:
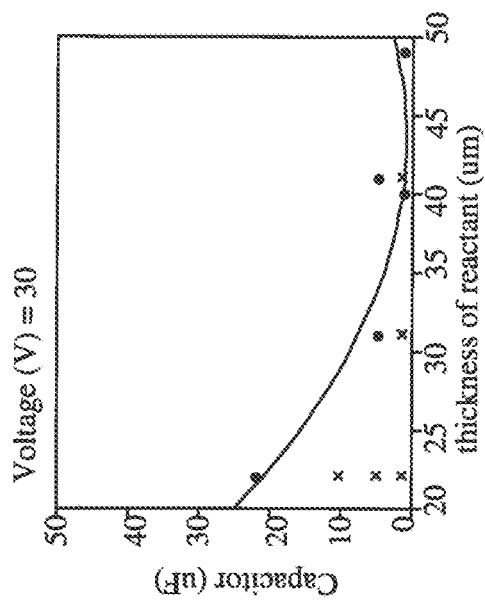

Using the same formulation described above, collected data demonstrated that higher voltage capacitors having lower capacitance would also readily ignite the solid fuel layer. This is demonstrated by the three graphs set forth in FIGS. 11A-11C.

Figure 12:
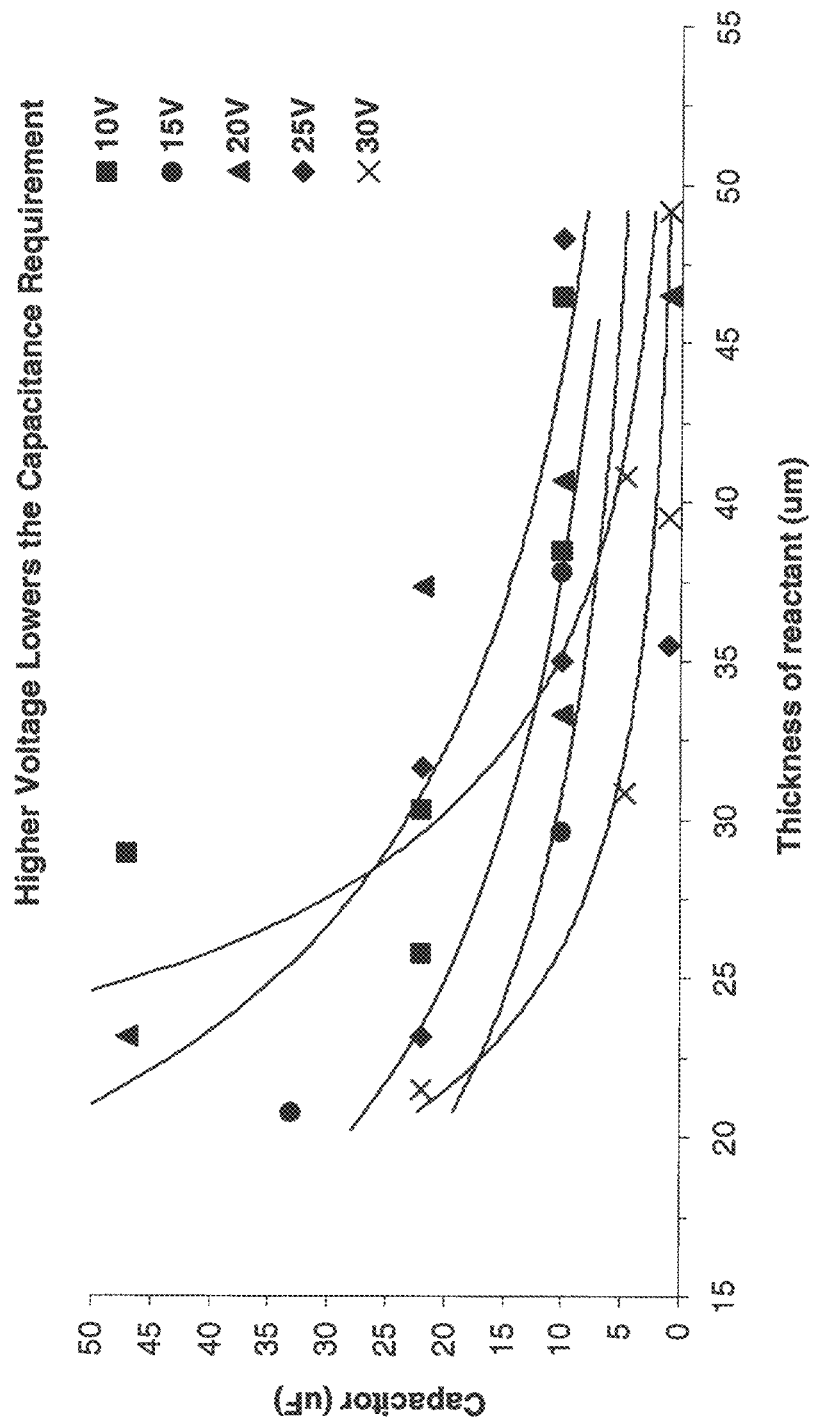
FIG. 12 is a graph of solid fuel thickness versus the capacitance of a capacitor at varying capacitor voltages.

FIG. 12 is a graph of thickness of the solid fuel (or reactant) to the capacitance of a capacitor for a variety of capacitor voltages, again using the same reactant formulation 66.24% Zr: 25.76% Fe2O3: 8% MnO2, percentages by dry weight ratio. This graph illustrates two things. First, using higher voltage capacitors lowers the required capacitance of the capacitors. Second, increasing the thickness of the reactant improved activation. However, it should be noted that at some point reactant thickness will inhibit activation. Activation energy was as low as 0.18 mJ.

Collected data set forth in FIG. 13 showed that as the voltage of a capacitor increased the required capacitance of the capacitor decreased over a range of solid fuel thicknesses of approximately 20 µm to 49 µm. In addition, by varying reactant thickness and the voltage of the capacitor, the energy required to initiate the solid fuel could vary from as low as 0.2 mJ to 11.25 mJ. The heat units tested were two-sided heat units having a steel lead contacting the solid fuel. The heat units incorporated the reactant formulation: 66.24% Zr: 25.76% Fe2O3: 8% MnO2, percentages by dry weight ratio.

Heat units using a solid fuel capable of undergoing an exothermic metal oxidation-reduction reaction propagated without an igniter as disclosed and claimed herein dramatically reduce the number of components and processing steps required to make heat units and significantly reduces the cost. The heat units improve the safety of the device by eliminating a starter which typically generates high heat and potentially harmful gases. Heat units as described herein simplify the design and construction of multi-dose drug delivery devices. Furthermore, by simplifying and minimizing the elements necessary to activate oxidation-reduction reaction, the embodiments disclosed herein enhance the reliability of heat units and drug supply units utilizing the disclosed ignition system.

Various embodiments of the disclosure could also include permutations of the various elements recited in the claims as if each dependent claim was multiple dependent claim incorporating the limitations of each of the preceding dependent claims as well as the independent claims. Such permutations are expressly within the scope of this disclosure.

While the invention has been particularly shown and described with reference to a number of embodiments, it would be understood by those skilled in the art that changes in the form and details may be made to the various embodiments disclosed herein without departing from the spirit and scope of the invention and that the various embodiments disclosed herein are not intended to act as limitations on the scope of the claims. All references cited herein are incorporated in their entirety by reference.

What is claimed is:

1. A method of making a heating unit comprising:
   a) coating a portion of the interior surface of a conductive substrate with a slurry of solid fuel comprising a metal reducing agent, a metal containing oxidizing agent and an inorganic binder;
   b) solidifying a slurry;
   c) coupling a first electrode to the conductive substrate; and
   d) coupling a second electrode to the surface of the solid fuel.

2. The method of claim 1 wherein the metal reducing agent is selected from at least one of the following: zirconium, titanium, aluminum and iron.

3. The method of claim 1 wherein the metal containing oxidizing agent is selected from at least one of $MoO_3$, $Fe_2O_3$, $MnO_2$, $KClO_4$ and $KClO_3$.

4. The method of claim 1 wherein the binder is an inorganic silicate-based binder.

* * * * *